United States Patent [19]
Leonhardt et al.

[11] Patent Number: 5,713,917
[45] Date of Patent: Feb. 3, 1998

[54] APPARATUS AND METHOD FOR ENGRAFTING A BLOOD VESSEL

[76] Inventors: Howard J. Leonhardt, 13794 NW. 4th St., Bldg. #210 and #211, Sunrise, Fla. 33325; Syde A. Taheri, 268 Dan Troy, Williamsville, N.Y. 14221; Trevor Greenan, 13794 NW. 4th St., Bldg. #210 and #211, Sunrise, Fla. 33325

[21] Appl. No.: 710,460
[22] Filed: Sep. 18, 1996

Related U.S. Application Data

[63] Continuation-in-part of Ser. No. 549,880, Oct. 30, 1985, Pat. No. 5,591,195.
[51] Int. Cl.⁶ ................................................ A61M 29/00
[52] U.S. Cl. ...................................... 606/194; 606/198
[58] Field of Search ................................. 606/192, 193, 606/194, 195, 198; 623/1, 12

[56] References Cited

U.S. PATENT DOCUMENTS

| | | | |
|---|---|---|---|
| 5,342,348 | 8/1994 | Kaplan | 606/198 |
| 5,618,301 | 4/1997 | Hauenstein et al. | 606/198 |

*Primary Examiner*—Michael Buiz
*Assistant Examiner*—Kevin Truong

[57] ABSTRACT

An apparatus and method for engrafting a blood vessel are disclosed. The apparatus includes a tubular graft having radially compressible annular spring portions for biasing proximal and distal ends of the graft into conforming fixed engagement with an interior surface of the vessel, with bifurcated and adjustable length embodiments being disclosed. Apparatus for deploying the graft includes an insertion catheter having a nitinol core wire, a controllable tip balloon at a remote end thereof for dilation and occlusion of the vessel, and a controllable graft balloon in the vicinity of the tip balloon for fixedly seating the spring portions into conformance with the interior surface of the vessel. A spool apparatus for adjusting or removing an improperly placed graft, and a micro-emboli filter tube, are usable with the deployment apparatus. A method of percutaneously implanting a graft, including a single-entry method for percutaneously implanting a bifurcated graft, are also disclosed.

28 Claims, 15 Drawing Sheets

APPARATUS AND METHOD FOR ENGRAFTING A BLOOD VESSEL

The present application is a continuation-in-part of application Ser. No. 08/549,880 filed Oct. 30, 1995 now, U.S. Pat. No. 5,591,195.

BACKGROUND OF THE INVENTION

A. Field of the Invention

The present invention relates to blood vessel graft systems for repairing aneurysms, and more particularly to a catheter-based graft system for repairing aortic aneurysms by deploying a graft within a blood vessel via percutaneous entry into a femoral artery of a patient.

B. Description of the Prior Art

An aortic aneurysm is a very common deteriorating disease typically manifested by weakening and expansion of the aorta vessel wall at a region between the aorto-renal junction and the aorto-iliac junction. Aneurysms affect the ability of the vessel lumen to conduct fluids, and may at times be life threatening, for instance when rupture of the vessel wall occurs. A standard treatment for repairing an aneurysm is to surgically remove part or all of the aneurysm and implant a replacement prosthetic section into the vessel, however such surgery is generally postponed until the aneurysm has grown to a diameter greater than five centimeters. With aneurysms over five centimeters in diameter, the risk of complications is greater than the risks inherent in surgical excision and grafting of the aneurysm. Consequently, aortic aneurysms measuring greater than five centimeters in diameter, and those showing a rapid increase in size, are generally surgically removed and grafted as a matter of course, before rupture occurs.

The standard procedure for repairing an aortic aneurysm requires one or two days of preparing the large and small intestines prior to hospitalization. The operation itself generally takes one to three hours to perform, and necessitates several units of blood for transfusion. The patient commonly remains hospitalized for several days following surgery, and requires as much as three months recuperation time before returning to work. Moreover, there remain significantly high rates of mortality and morbidity associated with the standard procedure. The mortality rate is as high as eight percent, while the morbidity rate includes incident complications such as blood loss, respiratory tract infections, wound infections, graft infections, renal failure, and ischemia of the bleeding intestine. The mortality and morbidity rates for this type of major surgery are also often influenced by the fact that the typical aortic aneurysm patient is elderly and therefore less able to withstand major surgery, including anesthesia.

Other treatments for repairing an aneurysm involve deploying a graft device at the aneurysm site via a catheter travelling through a femoral artery. Conventional tubular aortic replacement sections, however, are generally considerably larger in diameter than the femoral artery and therefore cannot be inserted through the femoral artery lumen to the site of the aneurysm. Expandable graft devices suitable for catheter delivery and deployment have been proposed, as in U.S. Pat. Nos. 4,140,126 and 4,562,596 by Choudhury and Kornberg, respectively, however the expanding structures of the devices are cumbersome and difficult to operate.

U.S. Pat. No. 5,104,399 to Lazarus discloses an artificial graft device having staples at proximal and distal ends thereof for fixing the graft within the vessel, and a catheter-based deployment system including a tubular capsule from which the graft is deployed. The graft is of a preselected cross section and length, and is capable of being substantially deformed so as to accommodate to the interior surface of the blood vessel.

The majority of other graft systems, as exemplified by U.S. Pat. Nos. 5,304,220 to Maginot and 5,151,105 to Kwan-Gett, require additional suturing or other methods for securing a graft. Furthermore, once a graft has been placed inside the lumen, adjustment usually requires a major surgical procedure.

Furthermore, the prior art stainless steel or elgialloy stent grafts carry high leakage rates. Moreover, high incidence of fractures have been associated with stainless steel stent grafts.

An additional problem with grafts in the public domain is the graft in-folding which causes leakage, migration, and thrombosis. Too, those grafts in the public domain such as bearing U.S. Pat. No. 5,507,771 can provide adequate seals only with straight surfaces due to the spring shape and sealing force.

In cases where the aneurysm involves the ipsilateral and contralateral iliac vessels extending from the aorta, it is known to provide a generally Y-shaped bifurcated graft having a primary limb joining with an ipsilateral limb and a contralateral limb. An example of such a graft, and means for surgically implanting same, are described in U.S. Pat. No. 5,387,235 to Chuter. The surgical procedure taught by Chuter involves either surgical isolation of the femoral vessels in the groin to provide direct access to the vessels, or percutaneous entry through both ipsilateral and contralateral femoral arteries.

The difficulties involved with traditional surgical procedures and additional complexities associated with securing grafts make the treatment of aneurysms a very expensive and lengthy procedure. Thus, there exists a need for a treatment for aneurysms which requires minimal preparation and outpatient care, and which provides a safe and percutaneous method for deploying a graft capable of remaining in place without additional suturing or stapling for security.

SUMMARY OF THE INVENTION

Therefore, it is an object of the present invention to provide a graft which is deployable percutaneously by low-profile deployment means, and which provides a leak-proof conduit through the diseased region without suturing or stapling.

It is another object of the present invention to provide a bifurcated graft deployable through a single entry site.

It is yet another object of the present invention to provide an adjustable-length extension graft for coupling with a limb of a previously deployed graft.

It is yet another object of the present invention to provide low-profile graft deployment means capable of securely deploying a graft via percutaneous entry.

It is yet another object of the present invention to provide deployment means having inflatable and deflatable balloons for modeling a graft spring portion into conforming fixed engagement with the interior surface of a vessel, for dilating a vessel to facilitate insertion, and for controlling blood flow through a vessel during deployment of a graft.

It is yet another object of the present invention to establish an improved method for securely deploying a graft with minimal incision.

It is yet another object of the present invention to establish a method for implanting a graft with low mortality and low morbidity risks to patients.

It is yet another object of the present invention to establish a method for implanting a graft which requires less hospital and outpatient care than required by normal surgical grafting procedures.

It is yet another object of the present invention to establish a single-entry method for deploying a bifurcated graft.

It is yet another object of the present invention to provide means for easily adjusting or removing an improperly deployed graft.

The present invention relates to an aneurysm repair system characterized by a graft apparatus which can be placed percutaneously via deployment means at the location of an aneurysm. It will be understood the term "proximal" as used herein means relatively closer to the heart, while the term "distal" as used herein means relatively farther from the heart.

The graft apparatus of the present invention comprises a tubular graft formed of bio-compatible graft material for conducting fluid, and may be in the form of either a straight single-limb graft or a generally Y-shaped bifurcated graft having a primary limb joining with a pair of lateral limbs, namely an ipsilateral limb and a contralateral limb, at a graft junction. A single-limb extension graft having a mating portion for coupling with a lateral limb of a bifurcated graft and an adjustable length portion extending coaxially from a distal end of the mating portion is also within the scope of the present invention. The graft material, preferably thin wall woven polyester or Polytetrafluoroethylene (PTFE), is chosen so that the graft is capable of substantially deforming to conform to an interior surface of the blood vessel, and is preferably tapered through a middle portion of each limb. Other covering materials may be used, however, including microporous polyurethane, lycra, or cryogenically preserved explanted veins. The most preferred embodiment for the covering material is Lycra outside with thin PTFE inside at top proximal section with bare nitinol zig-zag extension for above renal artery fixation. Further, for the aortic section, having aortic wall movement of approximately 3 MMS per heart beat, polyester (Dacron) is the preferred covering material. Moreover, with respect to grafts used in the iliac artery sections, where there is very little wall movement, PTFE is the preferred graft covering material. In the adjustable length portion of the extension graft, the graft material is crimped to permit axial or lengthwise extension and compression thereof.

The graft apparatus includes radially compressible spring means, preferably in the form of a nitinol wire spring having a pair of coaxially spaced annular spring portions connected by a connecting bar, for biasing proximal and distal ends of an associated graft limb or limb portion radially outward into conforming fixed engagement with the interior surface of the vessel. In the extension graft, an unpaired annular spring portion is located at a distal end of the adjustable length portion for similar biasing purposes. Each wire spring is enclosed by the graft material and stitched thereto, with cut-out portions being provided between spokes of the wire spring to define a plurality of radially distensible finger portions at the ends of the graft. A distal end of the contralateral limb of the bifurcated graft, and the distal end of the adjustable length portion of the extension graft, are each provided with a retainer ring to retain respective spring portions associated therewith in a radially compressed or loaded condition during deployment.

In a preferred embodiment, the graft apparatus further comprises a plurality of outer packets formed of a light degradable polymer and containing a tissue adhesive which is released by fiber-optic scope after the graft is implanted to bond the ends of the graft to the interior surface of the vessel and prevent leakage through micro-cracks therebetween. Medical grade expandable foam cuffs preferably surround the middle portion of the graft to promote clotting within the aneurysm sac. Alternatively, light actuated cryo precipitate fibrin glue may be painted onto the exterior surface of the graft material with a brush. The adhesive naturally remains as syrup until light actuates and cures. This replaces the need for packets and reduces the possibility of premature release of adhesive from packets that may break during deployment.

The deployment means of the present invention generally comprises an elongated sheath introducer having an axially extending sheath passage for slidably receiving the graft and maintaining the graft and associated spring means in a radially compressed pre-loaded condition prior to deployment of the graft within the vessel lumen, an elongated insertion catheter received within the sheath passage and pre-loaded graft for use in guiding the graft to the location of the aneurysm and deploying the graft within the vessel lumen at such location, and a flexible condensing spring push rod slidably arranged about the insertion catheter and received within the sheath passage to abut with the graft for navigating through tortuous vessels and pushing the graft out of the sheath passage during deployment. Deployment means may also comprise a micro-emboli filter tube selectively slidable over the sheath introducer and having controllable renal and iliac filters which may be opened to catch thrombus dislodged into the blood stream.

The insertion catheter of the present invention includes an embedded kink-resistant nitinol core wire and three inner tracks extending lengthwise thereof. A first inner track opens at both a near end and a remote end of the insertion catheter for receiving a guidewire to guide the insertion catheter through the vessel lumen. A second inner track opens at the near end of the insertion catheter for allowing fluid communication with an inflatable and deflatable tip balloon located at the remote end of the insertion catheter for dilating the vessel ahead of the graft and controlling blood flow through the vessel during placement. A third inner track opens at the near end of the insertion catheter for allowing fluid communication with an inflatable and deflatable graft balloon located near the remote end of the insertion catheter generally for securing the graft spring means against the interior surface of the vessel during graft deployment.

An optional spool apparatus may also be incorporated into the deployment means for collapsing a deployed graft and reloading the graft into sheath introducer 106 if unexpected leakage is observed due to incorrect graft position or size. The spool apparatus is connected to the sheath introducer and includes a plurality of suture loops wound around a spool cylinder and arranged to extend through a central axial passage of the push rod and around respective crests of a distal spring portion of the graft. A hand crank enables rotation of the spool cylinder to collapse the distal spring and pull it to within the sheath introducer, and a blade is provided on the spool apparatus for cutting each suture loop at one point to permit removal of the suture material if repositioning or removal of the graft is unnecessary.

A method of surgically implanting a pre-sized single limb graft to repair a previously-mapped aortic aneurysm using the deployment means of the present invention may be summarized as follows, keeping in mind that fluoroscopic or other monitoring means known in the art may be employed throughout the procedure.

First, a guide wire is introduced into the vessel via a femoral percutaneous entry and progressively inserted until a remote end of the guide wire extends upward past the aorto-renal junction, and the insertion catheter with surrounding pre-loaded graft, push rod, and sheath introducer are caused to follow the guidewire through the vessel lumen using the first inner track of the insertion catheter until the tip balloon is above the aorto-renal junction. The tip balloon may be partially inflated during insertion of the deployment means to dilate the vessel for easier introduction, and once properly positioned, may be inflated further so as to obstruct blood flow in the aorta just above the aorto-renal junction. With aortic blood flow obstructed, the insertion catheter is rotated so that the sheath introducer and compressed graft therewithin are best aligned to match the bends in the patient's aorta. Next, the spring portion associated with the proximal end of the graft is observed for correct axial alignment within the vessel at a location just below the aorto-renal junction.

Once proper positioning and alignment of the apparatus are observed, the sheath introducer is withdrawn a short distance while holding the push rod in place to release the proximal spring portion of the graft from within a remote end of the sheath passage and allow it to expand radially outward to conform with the interior surface of the vessel, with verification being made that the proximal spring portion continues to be in correct position. The operator may remove the guidewire from the first inner track and inject contrast media into the first inner track, or may place an ultrasound imaging catheter, for purposes of visualization. Next, the insertion catheter is moved upward within the vessel to align the graft balloon to within the proximal spring portion of the graft, and the graft balloon is inflated with relatively high pressure to fixedly model the proximal spring portion against the interior surface of the vessel. The sheath introducer may now be withdrawn further to fully deploy the graft, including the distal spring portion, which should be located at a healthy region below the aneurysm.

Blood flow may then be gently introduced to the graft by slowly deflating the tip balloon. The graft balloon may be repeatedly deflated, moved incrementally along the central axis of the graft, and re-inflated to smooth out any wrinkles in the graft material. When the graft balloon has traveled down the graft to within the distal spring portion, it may again be inflated at a relatively high pressure to fix the distal spring in conformance with the inner surface of the vessel. If it is observed that the graft is not in its intended position, the spool apparatus of the present invention may be used to reload the graft within the sheath introducer.

Once the graft is correctly deployed, the deployment means may be completely withdrawn from the patient, and a fiber-optic scope inserted through the entry site to direct light at the tissue adhesive packets to cause the packet polymer material to degrade, thereby releasing the tissue adhesive. Finally, the entry site attended using standard procedure. Post-operative imaging may be conducted to verify isolation of the aneurysm, with particular attention being given to the occurrence of leaks at the proximal end of the graft closest to the heart.

The present invention also relates to a single-entry method of surgically implanting a pre-sized bifurcated graft in cases where mapping of the aneurysm indicates involvement of one or both iliac vessels.

Deployment of the bifurcated graft is carried out by a method similar to that used to implant a single-limb graft, except that additional procedures are required to properly implant a contralateral limb of the bifurcated graft within a contralateral iliac vessel. As the sheath introducer is withdrawn to deploy the primary leg of the graft within the aorta, the contralateral limb of the graft will be released from the sheath introducer when the sheath introducer has been withdrawn just past the graft junction, such that the contralateral limb of the graft is within the aneurysm sac or directed downward into the contralateral iliac vessel. The retainer ring at the distal end of the contralateral limb prevents premature expansion of the spring portion associated with such end to permit proper positioning of the contralateral limb within the contralateral iliac vessel.

Positioning of the contralateral limb is carried out using the insertion catheter and a deflectable guide wire inserted within the first inner track of the insertion catheter and having an inflatable and deflatable tip balloon at a remote end thereof. First, the graft balloon is deflated and the insertion catheter with inserted deflectable guide wire are withdrawn to the graft junction. A dial control may be used to deflect the remote end of the guide wire and direct it into the contralateral limb of the graft; the guide wire is then advanced deep into the contralateral iliac vessel and the tip balloon thereof is inflated to anchor the guide wire within the vessel. With its own tip balloon partially inflated, the insertion catheter is advanced along the anchored guide wire into the contralateral limb of the graft. The insertion catheter tip balloon is then inflated more fully to allow flow direction of blood to carry graft material of the contralateral limb down the contralateral iliac vessel. The contralateral limb is moved to a final desired location by deflating the insertion catheter tip balloon and advancing it to within the spring portion at the distal end of the contralateral limb held by the retainer ring, partially re-inflating the tip balloon to hold the distal end and associated distal spring portion of the contralateral limb by friction, advancing the insertion catheter into the contralateral iliac vessel until the distal end of the contralateral limb is at the desired location, and finally reinflating the tip balloon fully to expand or break the retainer ring and release the spring portion. The deployment means may then be withdrawn and removed from the entry site and the entry site attended using standard procedure.

If the extent of disease indicates that a longer graft limb is necessary in either or both iliac vessels, an adjustable length extension graft may be coaxially coupled to a lateral limb, for instance the contralateral limb, of the bifurcated graft by the following procedure.

The extension graft is deployed via percutaneous entry through the contralateral femoral artery. A guide wire is directed through the contralateral limb and up into the primary limb of the bifurcated graft, and deployment means carrying a pre-loaded extension graft is directed over the guidewire to position the mating portion of the extension graft partially within the contralateral limb of the bifurcated graft such that a first spring portion at the proximal end of the mating portion is overlapped by the spring portion at the distal end of the contralateral limb. The sheath introducer may then be withdrawn while the push rod is held stationary to deploy the first spring portion, the insertion catheter moved upwards to locate the graft balloon within the first spring portion, and the graft balloon inflated to conform the first spring portion to the interior surface of the contralateral limb. Contrast media is injected through the first inner track of the insertion catheter to verify that the coupled graft limbs are not leaking. Next, the sheath introducer is further withdrawn to release a second spring portion defining a junction between the mating and adjustable-length portions, and a third spring portion at a distal end of the adjustable-length portion the radially retained distal annular spring of the adjustable length portion, into the contralateral iliac vessel.

The graft balloon is then deflated and moved downward to within the third spring portion, and partially re-inflated to hold the distal end of the adjustable-length portion by friction. This permits the distal end of the adjustable-length portion to be positioned generally just above the sub-iliac or hypo-gastric branch by withdrawing the insertion catheter downward. The third spring portion is deployed by fully reinflating the graft balloon therewithin to expand or break the surrounding retainer ring and fix the third spring portion in conformance with the interior surface of the vessel. Any wrinkles in the extension graft may be removed using the graft balloon. Finally, once leakage has been ruled out, such as by angiogram verification, the deployment means may be withdrawn and the entry site attended.

BRIEF DESCRIPTION OF THE DRAWINGS

The nature and mode of operation of the present invention will now be more fully described in the following detailed description taken with the accompanying drawings wherein.

DETAILED DESCRIPTION OF THE PREFERRED EMBODIMENTS

Figure 1:
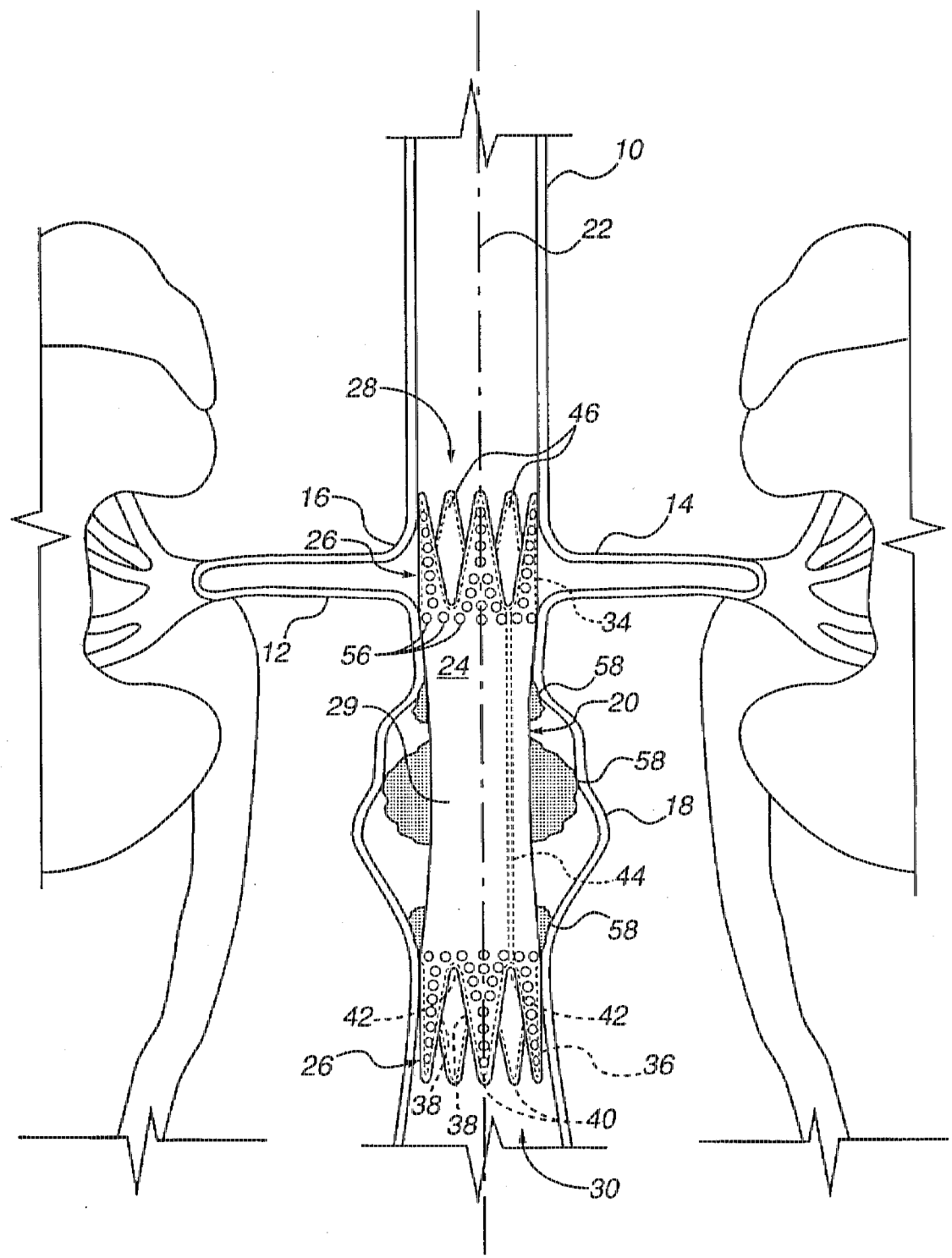
FIG. 1 is an elevational view showing a single-limb graft of the present invention fully deployed within an aorta of a patient to repair an aneurysm.

Referring initially to FIG. 1, there is shown an aorta 10 joined by renal arteries 12 and 14 at aorto-renal junction 16, and having an aneurysm 18 below the aorto-renal junction characterized by a weakened and expanded vessel wall at the diseased region. In accordance with the present invention, an elongated single-limb tubular graft 20 is deployed at the region of aneurysm 18 as a prosthetic device for the purpose of relieving blood flow pressure against the weakened vessel wall by acting as a fluid conduit through the region of the aneurysm. In its deployed condition, graft 20 defines a central longitudinal axis 22 extending in a direction of blood flow through aorta 10, and generally comprises a deformable graft material 24 enclosing radially compressible spring means 26 for biasing a proximal end 28 and a distal end 30 of the graft into conforming fixed engagement with an interior surface of aorta 10.

Graft material 24 is a biocompatible, flexible and expandable, low-porosity woven fabric, for example thin-walled polyester or PTFE, capable of substantially deforming to conform with an interior surface of aorta 10, and additionally capable of acting as a fluid conduit when in tubular form. A middle portion 29 of graft 20 between proximal end 28 and distal end 30 is tapered to provide a decreased fluid-conducting cross-sectional area relative to ends 28 and 30, such as by excising at least one longitudinal strip of graft material 24 and sewing the resulting gap or gaps closed, as a way of reducing the occurrence of folding and wrinkling and adapting the graft to fit within a wider range of differently sized vessels.

Enclosed within graft material 24 is a nitinol wire spring having a proximal spring portion 34 and a distal spring portion 36. Spring portions 34 and 36 are designed to exert radially outward force of approximately 240 to 340 grams for biasing graft material 24 at graft ends 28 and 30 into conforming fixed engagement with the interior surface of aorta 10 above and below aneurysm 18. The nitinol wire used to form the spring is in a super elastic, straight annealed condition and may be coated with titanium oxide to improve biocompatibility, reduce the incidence of allergic reaction to nickel, and improve radiopacity. A PTFE coating may also be used to lower the risks of blood clotting and wire corrosion. As a further preventive measure, the coating may be treated with iridium 192 or other low dose Beta radiation emitting substance to reduce post-surgical cell proliferation in the vessel which can lead to closure of the vessel. Spring portions 34 and 36 are each formed by revolving a zig-zag wire pattern of straight spokes 38 connected by rounded alternating crests 40 and troughs 42 about central axis 22 to provide a continuous annular spring portion. A preferred spring portion includes five equispaced crests 40 and five equispaced troughs 42 formed to a predetermined radius to produce better spring properties and avoid sharp transitions in the wire, in that sharp transitions are more prone to failure. The coaxially spaced spring portions 34 and 36 are connected by at least one straight connecting bar 44 which preferably extends generally parallel to central axis 22 for minimal disruption of blood flow. Connecting bar 44 provides torsional stability for graft 20, and may be welded to spring portions 34 and 36, or fastened thereto by a small tightened sleeve (not shown).

Figure 2:
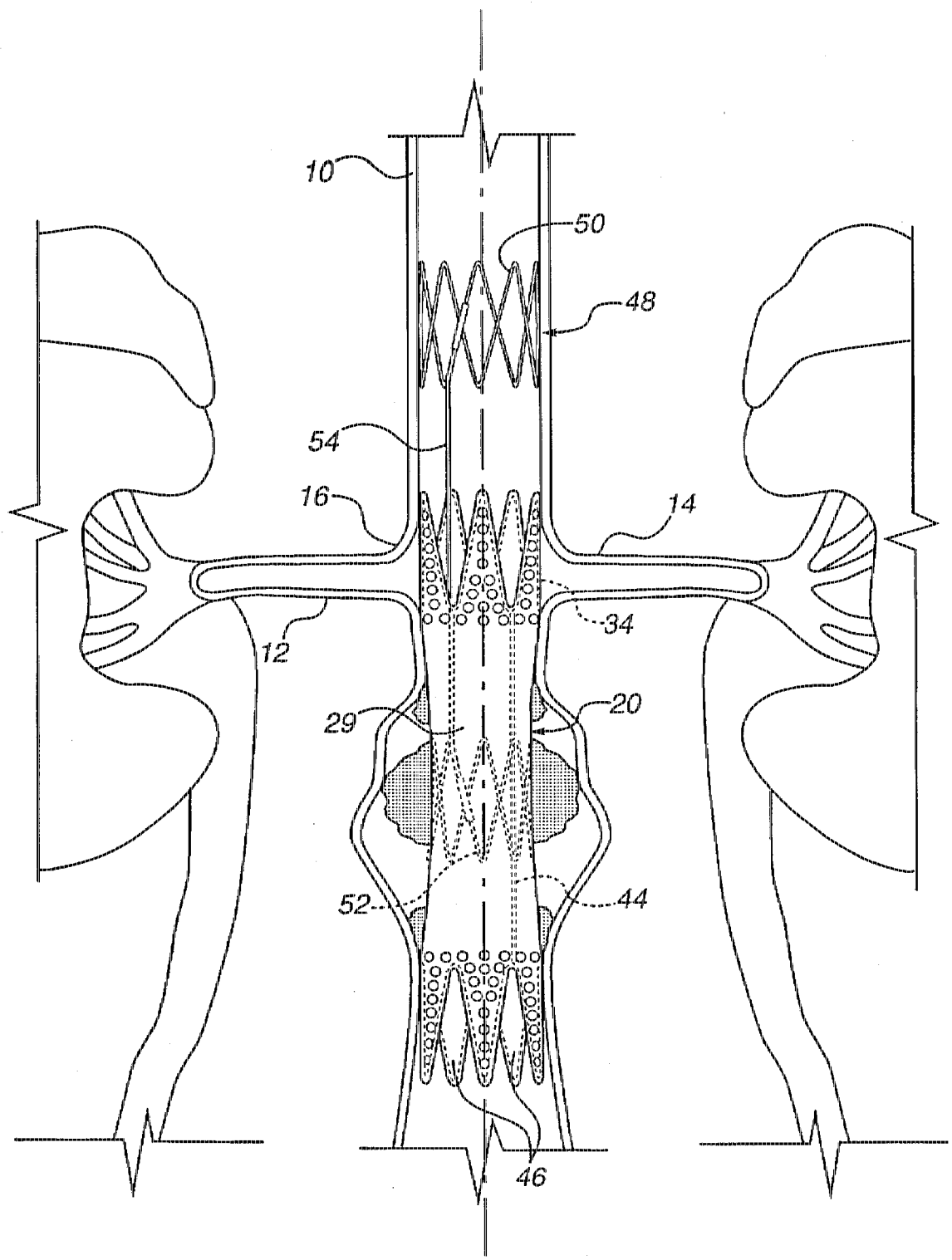
FIG. 2 is a view similar to that of FIG. 1, however showing an optional anchor spring attached to the graft for suprarenal fixation of the graft.

The wire spring is sewn within graft material 24 using polyester suture. Prior to sewing, graft material 24 is arranged to surround the wire spring and is heat pressed to conform to spring portions 34 and 36 using an arcuate press surface (not shown) heated to approximately 150 degrees Fahrenheit and corresponding in curvature to the spring portions. A preferred stitch pattern includes two generally parallel stitches extending along opposite sides of the wire, and a cross-over stitch around the wire for pulling the parallel stitches together to achieve tight attachment of graft material 24 to the wire spring. This method of attachment substantially prevents contact between wire spring and the interior surface of the vessel, and is reliable over time. In accordance with the present invention, graft material 24 is cut out between crests 40 of proximal spring portion 34 and distal spring portion 36 to define a plurality of radially distensible finger portions 46 at graft ends 28 and 30. Importantly, finger portions 46 allow graft 20 to be situated with proximal end 28 much closer to aorto-renal junction 16 than was possible with prior art graft constructions, since gaps between the finger portions may be aligned with renal arteries 12 and 14 so as not to block blood flow. Moreover, finger portions 46 may be radially compressed to approximate a conical tip to facilitate loading insertion of graft 20 within a sheath introducer, to be described hereinafter. As shown in FIG. 2, a bare nitinol wire anchor spring 48 may be used to provide increased positional integrity to graft 20 where healthy vessel neck between aorto-renal junction 16 and aneurysm 18 is particularly short. Anchor spring 48 includes a proximal spring portion 50 set approximately 20 mms above aorto-renal junction 16 for suprarenal fixation remotely of graft proximal spring portion 34, and a distal spring portion 52 sewn within graft middle portion 29 and connected to proximal spring portion 50 by at least one axially extending connecting bar 54. The provision of radially distensible finger portions 46 and optional anchor spring 48 render the present invention useful in a much greater patient population relative to prior art graft systems, in that only about 5 mms of healthy vessel neck below the aorto-renal junction is required as compared with about 20 mms for prior art graft systems.

Graft 20 further includes a plurality of releasable tissue adhesive packets 56 fixed to an exterior surface of graft material 24 at ends 28 and 30 for establishing a fluid tight seal between graft material 24 and the inner wall of aorta 10. Packets 56 may be constructed of photosensitive polyurethane and filled with biocompatible tissue adhesive, for example fibrin glue or isobutyl 2 cyanoacrylate. The tissue adhesive remains secure during deployment, and may subsequently be released by directing a fiber-optic catheter light source at packets 56 from inside graft 20 to cause breakdown of the packet material. Tissue adhesive enters and occupies small micro-cracks existing between graft material 24 and the interior surface of aorta 10 to form a bonding fluid seal, thereby preventing the serious problem of leakage. An alternative to the described tissue adhesive packets is the use of light activated cryo precipitate fibrin glue painted on the exterior surface of the graft material.

In addition to tissue adhesive packets 56 at ends 28 and 30, one or more cuffs 58 comprising medical-grade expandable foam may be provided to surround middle portion 29 to promote clotting in the space of the aneurysm outside of graft 20. In a preferred embodiment, first and second cuffs expandable to approximately 4–10 mms greater than the graft diameter are arranged near spring portions 34 and 36, and a third cuff expandable to approximately 10–40 mms greater than the graft diameter is arranged intermediate the first and second cuffs. Cuffs 58 preferably include fetal endothelial cells, smooth muscle cells, or other living tissue cells and giloma growth factor in their respective foam matrices or light activated foaming particles to encourage healing near spring portions 34 and 36 and filling of aneurysmal sac 18 around middle portion 29.

Figure 3:
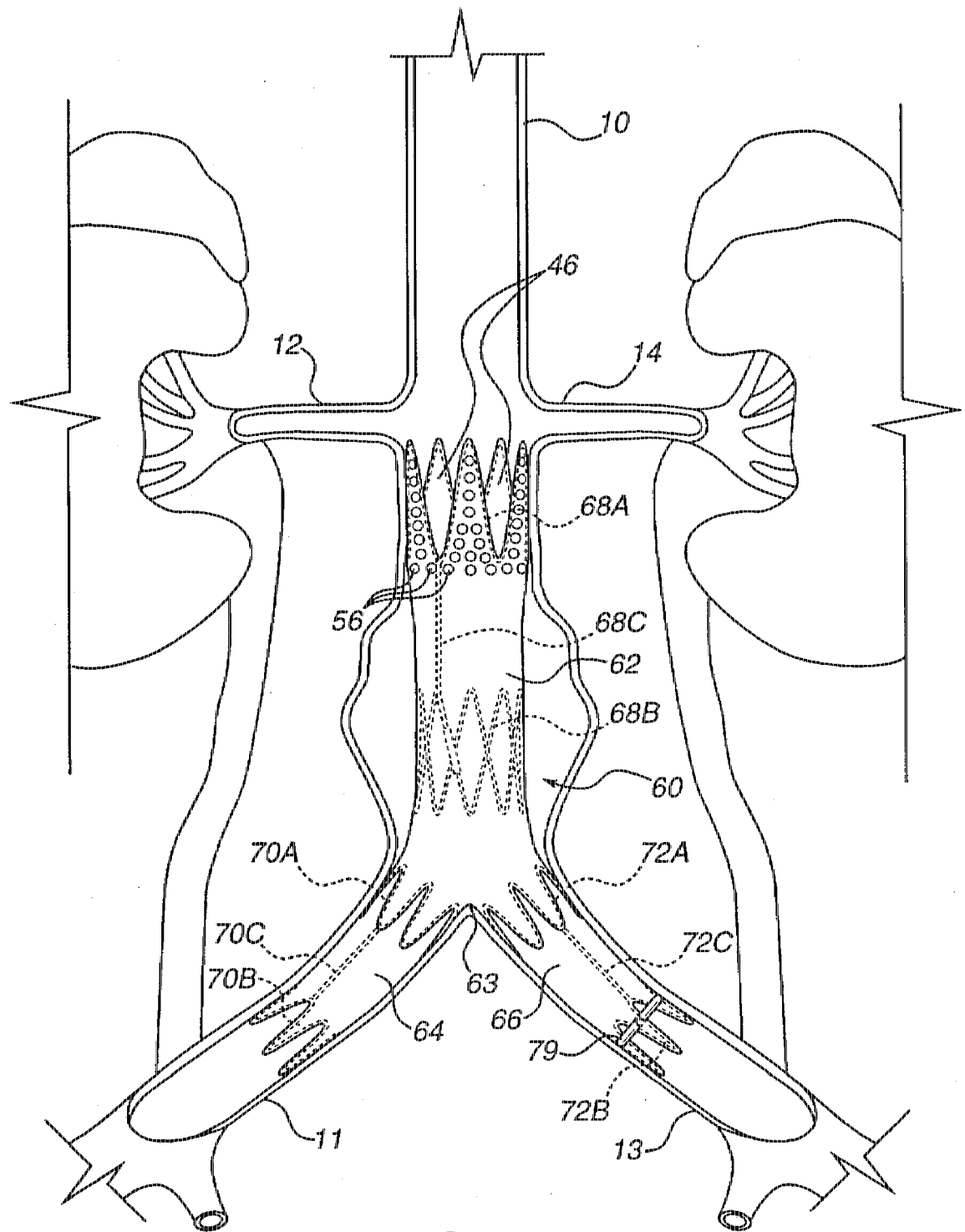
FIG. 3 is an elevational view showing a bifurcated graft of the present invention fully deployed within an aorta and lateral iliac vessels joined therewith.

A bifurcated graft 60 as shown in FIG. 3 is also within the scope of the present invention for use in cases where involvement of one or both iliac vessels 11 and 13 is indicated. Graft 60 is Y-shaped and includes a primary limb 62 for location within aorta 10, and is joined by an ipsilateral limb 64 for location within ipsilateral iliac vessel 11, and by a contralateral limb 66 for location within contralateral iliac vessel 13, at a graft junction 63. Each limb of bifurcated graft 60 is generally similar in construction to single-limb graft 20 in that the proximal and distal ends of each limb are biased into conforming fixed engagement with the interior surface of a corresponding vessel by annular spring portions associated therewith, and middle portions of each limb are preferably tapered. A first nitinol wire spring is enclosed by, and attachably sewn within, graft material 24 and includes a proximal spring portion 68A associated with a proximal end of primary limb 62, a distal spring portion 68B associated with a distal end of primary limb 62, and an axially extending connecting bar 68C coupling the proximal and distal spring portions together. Similarly, a second nitinol wire spring having a proximal spring portion 70A, a distal spring portion 70B, and an axially extending connecting bar 70C, is sewn within ipsilateral limb 64; and a third nitinol wire spring having a proximal spring portion 72A, a distal spring portion 72B, and an axially extending connecting bar 72C, is sewn within contralateral limb 66. Terminal ends of bifurcated graft 60, namely the proximal end of primary limb 62 and the distal ends of lateral limbs 64 and 66, are provided with radially distensible finger portions 46 as described above. Where entry is to be made through an ipsilateral femoral artery to deploy graft 60, distal spring portion 72B is held in a radially compressed condition by an expandable retainer ring 79, which may simply be a length of suture material tied end to end using a purse-string type knot to form a loop, to prevent premature deployment of distal spring portion 72B prior to proper positioning thereof within contralateral iliac vessel 13. Likewise, where entry is to be made through a contralateral femoral artery, distal spring portion 70B may be provided with a retainer ring 79 to prevent premature deployment of distal spring portion 70B prior to proper positioning thereof within ipsilateral iliac vessel 11. It will be understood that previously described tissue adhesive packets 56 and foam cuffs 58, while not shown in FIG. 3, may be incorporated into bifurcated graft 60. Specifically, packets 56 are preferably provided at least at the proximal end of primary limb 62 to prevent leaking, and foam cuffs 58 are preferably provided around the primary limb for filling aneurysmal sac 18.

Figure 4:
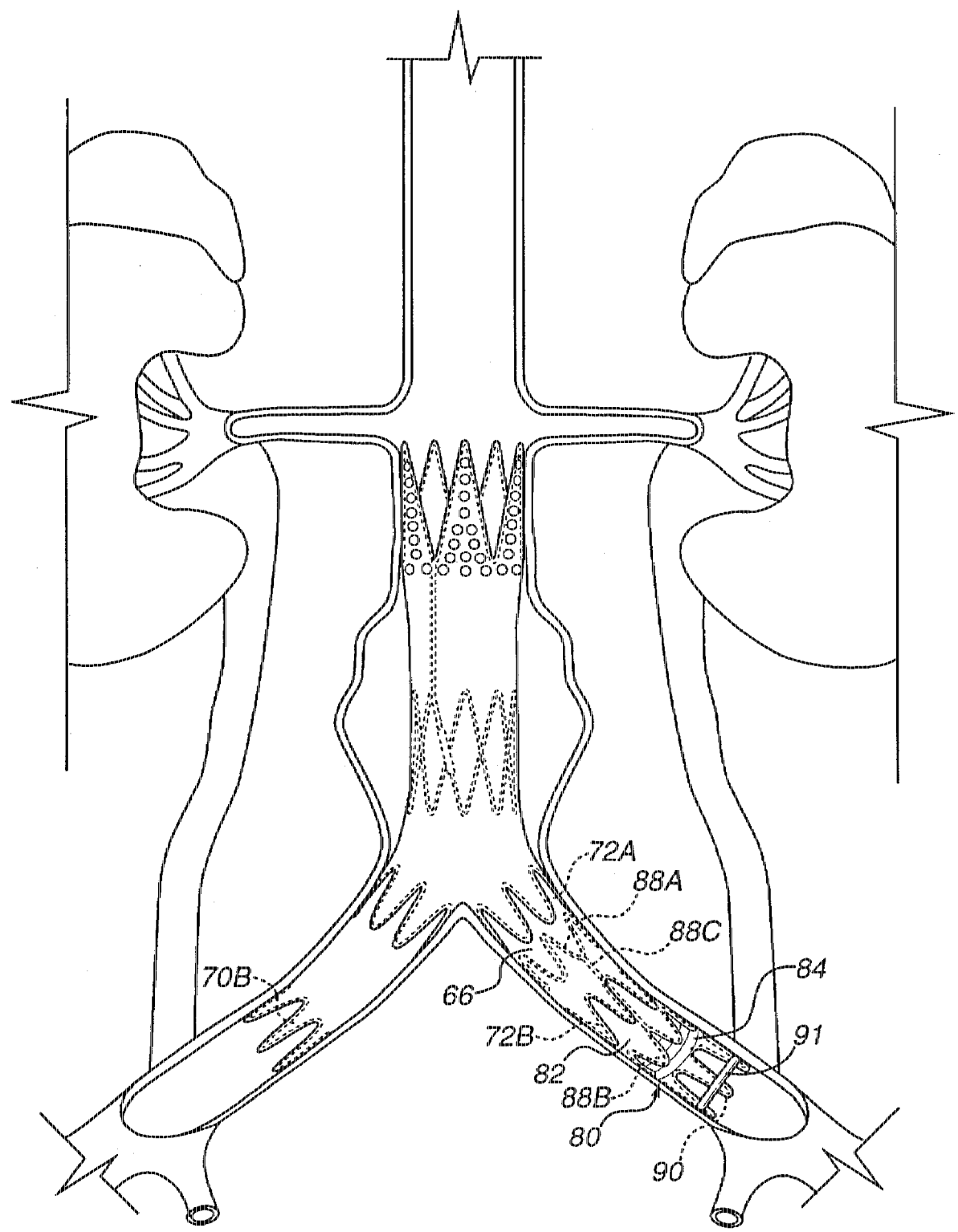
FIG. 4 is a view similar to that of FIG. 3, however showing an extension graft of the present invention for coupling with a lateral limb of the bifurcated graft.

A single-limb extension graft 80, as depicted in FIG. 4, embodies another useful apparatus of the present invention. Extension graft 80 is designed for end-to-end coupling with a lateral limb of bifurcated graft 60, for example contralateral limb 66, and generally includes a mating portion 82 and an adjustable length portion 84 extending coaxially from a distal end of the mating portion. Mating portion 82 includes a wire spring having a first spring portion 88A serving to bias a proximal end of mating portion 82 into conforming fixed engagement with an interior surface of contralateral limb 66, and a second spring portion 88B connected to first spring portion 88A by a connecting bar 88C serving to bias a distal end of mating portion 82 and a proximal end of adjustable length portion 84 into conforming fixed engagement with the interior surface of contralateral iliac vessel 13. An unpaired third spring portion 90 is provided at a distal end of adjustable length portion 84 to bias such end against the interior surface of contralateral iliac vessel 13, and is maintained in a radially compressed condition prior to deployment by a breakable retainer ring 91 similar to retainer ring 79. Third spring portion 90 is movable in opposite axial directions to a desired location during deployment by virtue of a crimped length of graft material provided in adjustable length portion 84.

As will be appreciated by those skilled in the art, the above described grafts 20, 60, and 80 may be manufactured in a range of sizes for fitting within differently sized vessels to repair aneurysms of various lengths.

Figure 5:
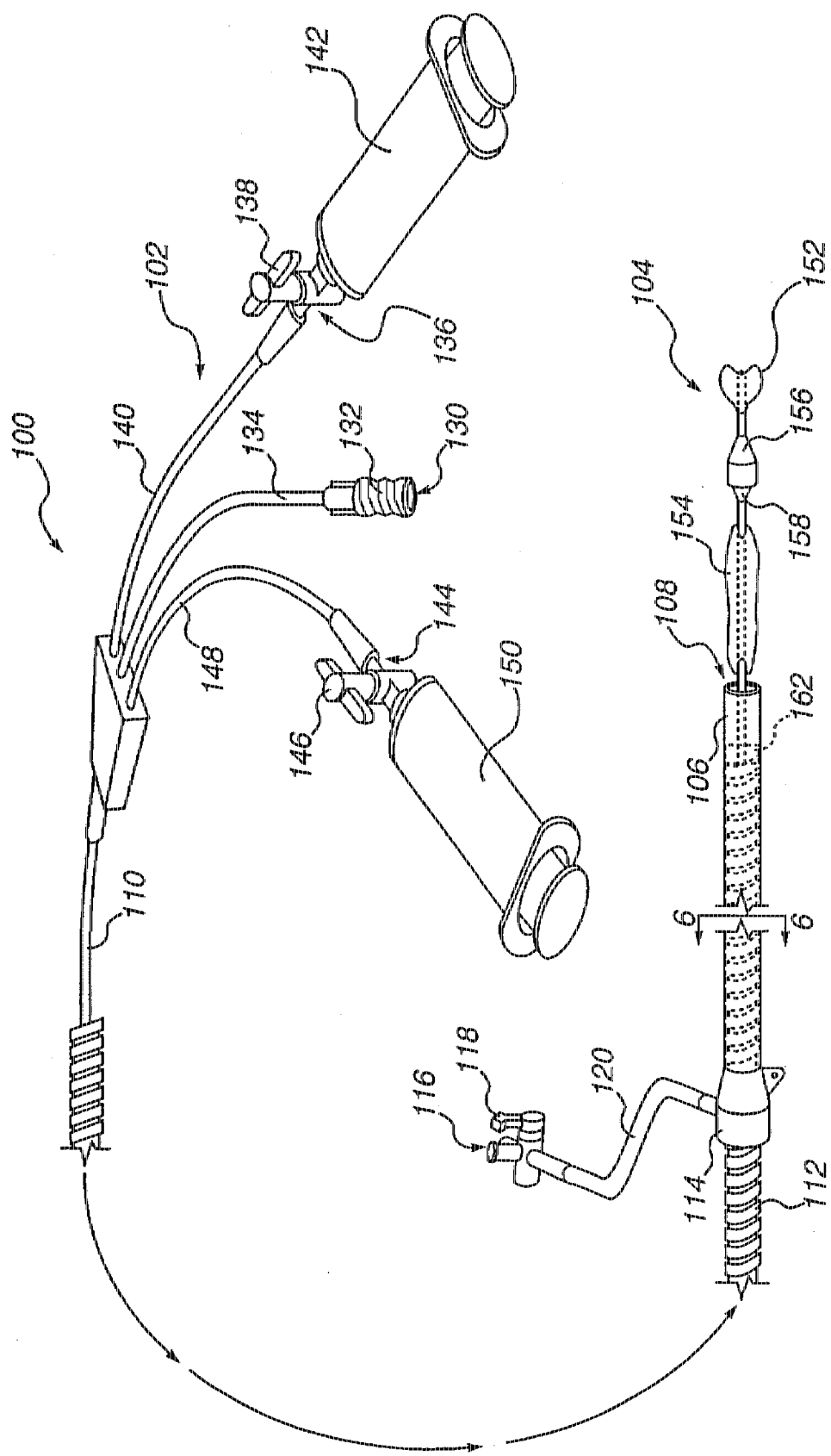
FIG. 5 is a perspective view showing graft deployment means of the present invention.
Figure 6:
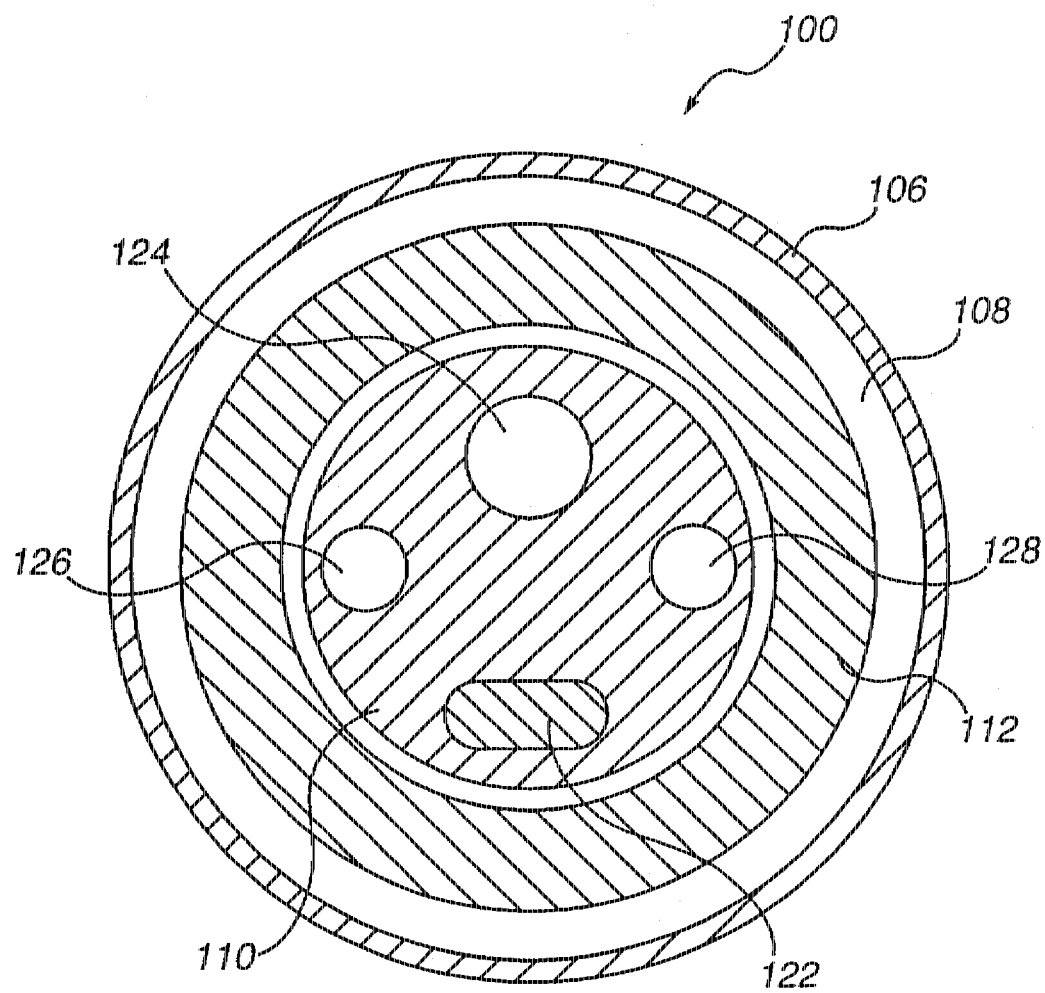
FIG. 6 is a sectional view thereof taken generally along the line 6—6 in FIG. 5.

A preferred apparatus of the present invention for deploying a graft within a blood vessel is depicted in FIGS. 5 and 6 and identified generally by the reference numeral 100. Deployment means 100 is elongated to permit delivery of a graft carried thereby to aneurysm 18 via percutaneous entry into a femoral artery of the patient, and may be described as having a near end 102 normally remaining outside the skin of the patient for manipulation by an operating surgeon, and a remote end 104 normally traveling inside the blood vessel lumen during deployment and carrying a graft to be implanted at aneurysm 18. Deployment means 100 includes an elongated sheath introducer 106 having an axially extending sheath passage 108; an elongated insertion catheter 110 loosely received within sheath passage 108; and an elongated compression spring push rod 112 slidably mounted over insertion catheter 110 and received within sheath passage 108.

Sheath introducer 106 is formed of a low-friction, flexible material, preferably F.E.P., however polyurethane, silicone, polyethylene, or other similar materials may be substituted for PTFE. The size of sheath introducer 106 is chosen based on the size of the graft to be deployed so as to hold the graft within a remote end of sheath passage 108 in a radially compressed, pre-loaded condition prior to deployment of the graft within the vessel, with sizes 12 FR, 14 FR, 16 FR, 18 FR, and 20 FR being suitable in a vast majority of instances. Graft finger portions 46 can be pushed together to approximate a conical tip for easier insertion of graft 20 within sheath passage 108, a feature which has resulted a 2 FR reduction in sheath introducer profile relative to loading a similar graft without finger portions 46. In order to permit viewing of a pre-loaded graft to confirm proper loading, sheath introducer 106 is preferably transparent. Sheath introducer 106 is equipped with at least one latex-lined hemostasis valve 114 at a near end thereof serving to form a fluid seal around push rod 112 to prevent blood from leaking out of the patient at the entry site. A side port means 116 is provided for transporting fluid, such as heparinized solution or contrast media, into sheath passage 108 and eventually into the blood vessel. Side port means 116 includes a manually operable valve 118 communicating with sheath passage 108 through a flexible tube 120 and adapted to receive a suitable fluid injection means (not shown).

Insertion catheter 110 which may be formed of 8 FR catheter tubing, is longer than sheath introducer 106 to permit near and remote ends thereof to extend from sheath introducer 106 when the insertion catheter is received within sheath passage 108. As seen in the cross-sectional view of FIG. 6, insertion catheter 110 is provided with an embedded, kink-resistant nitinol core wire 122, a first inner track 124, a second inner track 126, and a third inner track 128, all extending lengthwise thereof. Referring once again to FIG. 5, a first end port means 130 for transporting fluid to first inner track 124 includes a threaded adapter 132 for mating with suitable fluid injection means (not shown) and communicating with a near end of first inner track 124 through a flexible tube 134. A second end port means 136 for transporting fluid to second inner track 126 includes a manually operable valve 138 communicating with a near end of the second inner track through a flexible tube 140 and adapted to receive a suitable fluid injection means 142. Similarly, a third end port means 144 for transporting fluid to third inner track 128 includes a manually operable valve 146 communicating with a near end of the third inner track through a flexible tube 148 and adapted to receive a suitable fluid injection means 150.

In a preferred form of the invention, core wire 122 is gradually tapered from a diameter of 0.031 inches at the near end of insertion catheter 110 to a diameter of 0.020 inches at the remote end of the insertion catheter. This feature provides that the near end of insertion catheter 110 is strong, and the remote end of the insertion catheter is less likely to cause puncture or rupture of the vessel yet will not deflect significantly under force of blood flow. In addition to providing kink resistance and strength to insertion catheter 110, core wire 122 provides greatly improved torsional rigidity, whereby rotation at the near end of insertion catheter 110 about its longitudinal axis translates into a substantially equivalent rotation at the remote end of the insertion catheter, such that a graft may be easily rotated during deployment for proper alignment.

In accordance with the present invention, second inner track 126 communicates with a transparent polyurethane tip balloon 152 arranged circumferentially about insertion catheter 110 at the remote end thereof, while third inner track 128 communicates with a transparent polyurethane graft balloon 154 arranged circumferentially about insertion catheter 110 in the vicinity of tip balloon 152. Balloons 152 and 154 are preferably of the same outside diameter or profile when fully inflated, with graft balloon 154 being longer than tip balloon 152. Balloons 152 and 154 behave in a pressure compliant manner, such that the profile thereof may be continuously and reversibly varied by changing inflation pressure using fluid injection means 142 and 150, respectively. Fluid injection means may be a syringe having a slidable plunger for observably varying a plenum volume of the syringe, and the plenum volume may be functionally correlated with balloon profile diameter. A preferred inflation fluid is filtered carbon dioxide, which is readily visualized by X-ray observation.

Insertion catheter 110 further includes a tapered head 156 adjacent tip balloon 152 for providing a rigid vessel dilator characterized by a smooth atraumatic transition from an 8 FR profile of the insertion catheter to a larger profile of sheath introducer 106. Tapered head 156 preferably defines an annular abutment lip 158 arranged to engage the remote end of sheath introducer 106 to prevent withdrawal of the tapered head to within sheath passage 108. Insertion catheter 110 may also be provided with a plurality of circumferential radiopaque markings (not shown) equispaced along the length thereof to assist in location of the insertion catheter during deployment of a graft.

Push rod 112 is a metallic compression spring having a combination of flexibility and axial compression strength to enable it to follow the path of a tortuous vessel without loosing its ability to act as a push rod for exerting force against a graft during deployment. Push rod is sized with inner clearance relative to insertion catheter 110 and outer clearance relative to sheath introducer 106 so as to be independently movable within sheath passage 108. A plunger 162 is preferably arranged at remote end of push rod 112 for stopping blood flow within sheath passage 108. Push rod 112 may also include dampening means near its remote end, such as a thin heat-shrunken polyolifin or polyimid coating, to dampen undesirable recoil of the push rod.

Figures 7A, 7B:
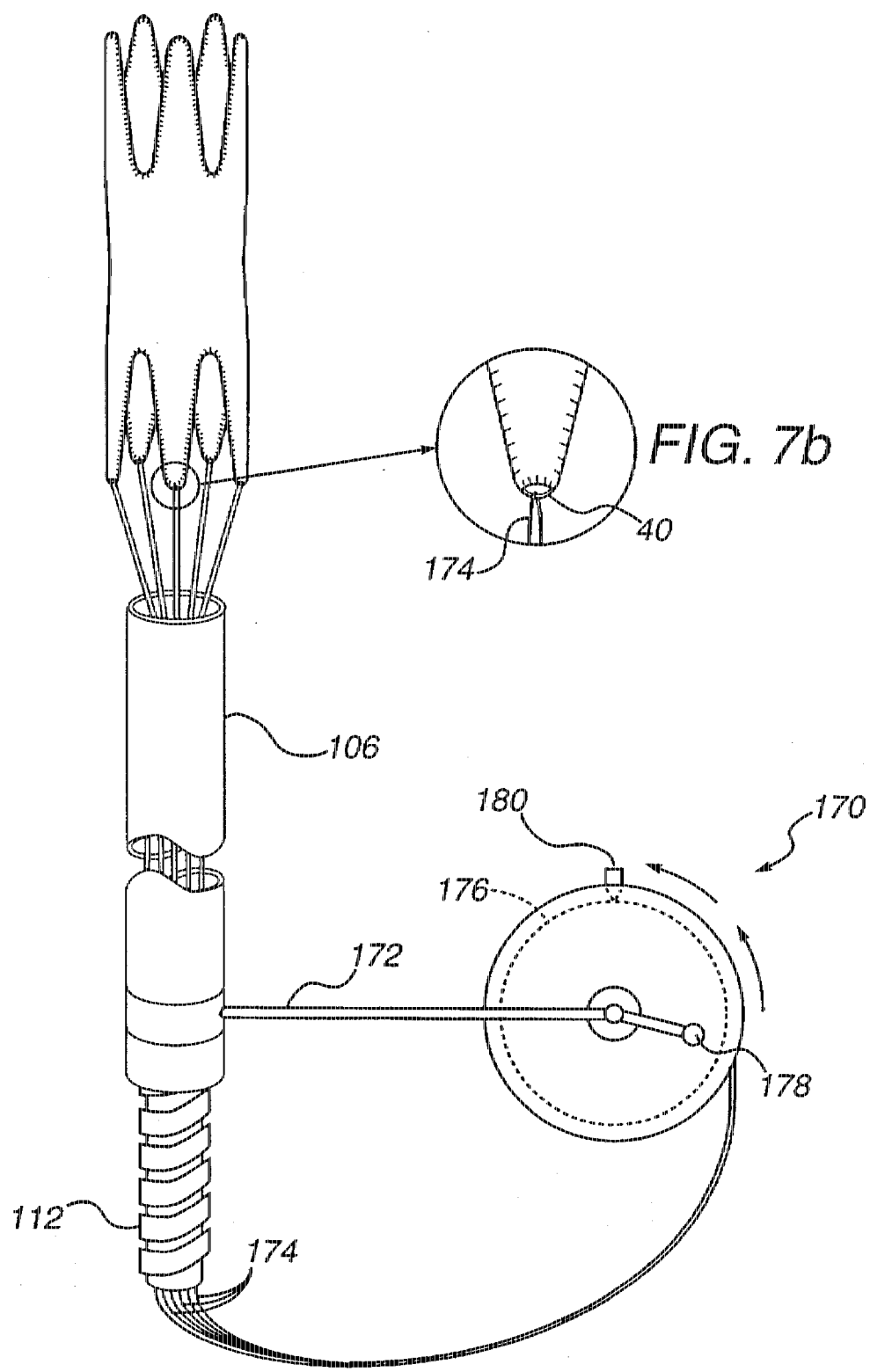
FIG. 7a is a perspective view showing a spool apparatus of the present invention.
FIG. 7b is an enlarged partial view of circled portion A in FIG. 7a showing the arrangement of a suture loop of the spool apparatus.

FIGS. 7a and 7b illustrate an optional spool apparatus 170 provided as part of deployment means 100 for collapsing a deployed graft and reloading the graft into sheath introducer 106 if unexpected leakage is observed due to incorrect graft position or size. Spool apparatus 170 is mounted adjacent a near end of sheath introducer 106 by a mounting arm 172, and includes a plurality of suture loops 174 wound around a spool cylinder 176 thereof and arranged to extend through a central axial passage of push rod 112 and around respective crests 40 of a distal spring portion of the graft, as depicted in FIG. 7b. A hand crank 178 and releasable pawl (not shown) are provided for rotating and fixing spool cylinder 176 of spool apparatus 170. A blade 180 is mounted on the body of the spool apparatus for selectively and simultaneously cutting each suture loop 174 at one point to enable removal thereof. Where optional spool apparatus 170 is provided, plunger 162 at the remote end of push rod 112 must be omitted to permit suture loops 174 to connect with the distal spring portion of the graft.

Figure 8:
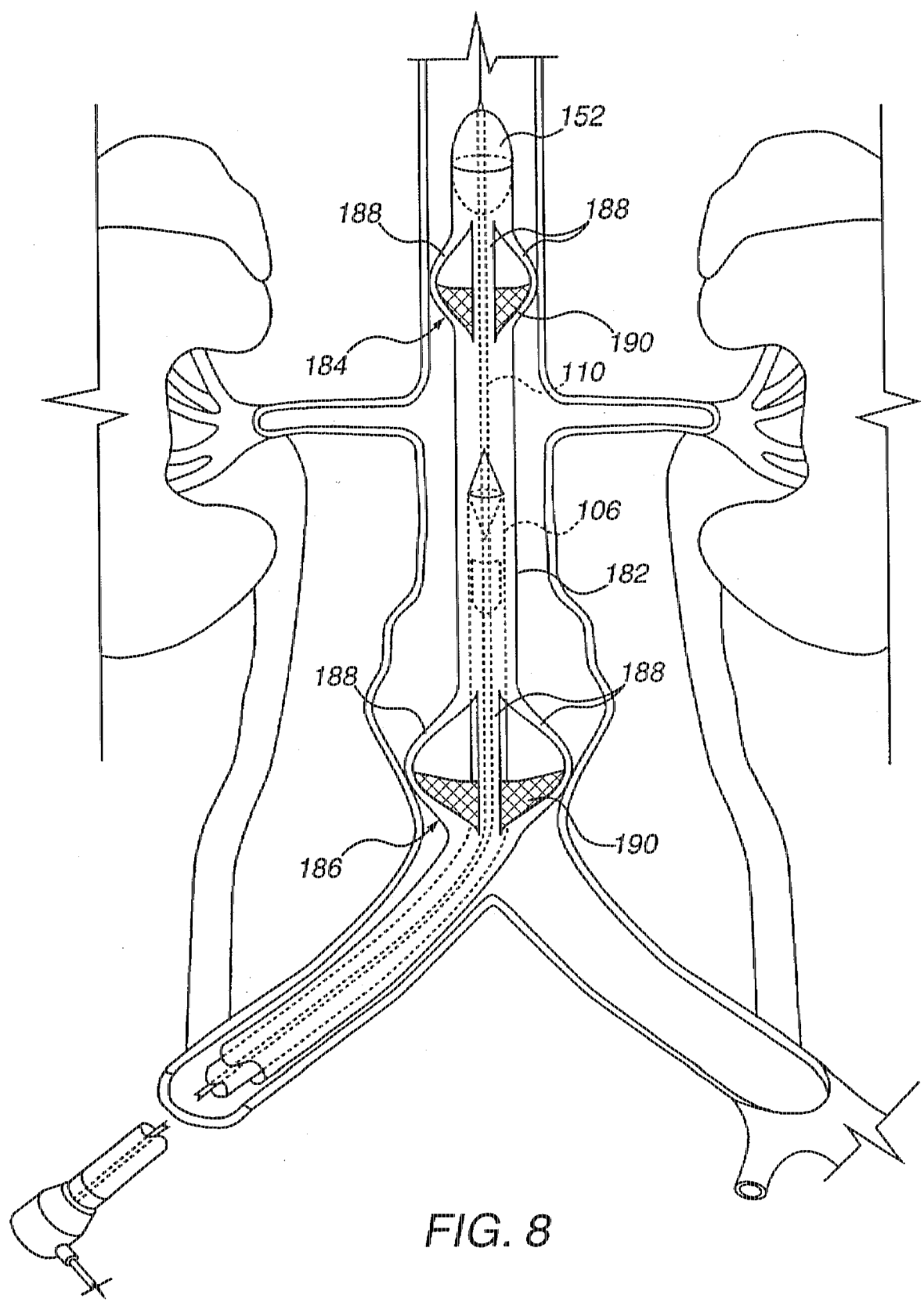
FIG. 8 is an elevational view showing a micro-emboli filter tube of the present invention in an activated condition.

FIG. 8 shows a micro-emboli filter tube 182 available for use with deployment means 100 of the present invention for trapping thrombus dislodged during manipulation of deployment means 100 within the vessel. Filter tube 182 is adapted to slide over sheath introducer 106 and includes a renal filter 184 and an iliac filter 186. Filters 184 and 186 are of similar construction and include a plurality of flexible spokes 188 defined by a series of axially extending slits spaced around the circumference of filter tube 182. Nylon mesh fabric 190 is affixed around the bottom portion of spokes 188, such that when filter tube 182 is axially compressed by pushing a near end thereof while a remote end thereof is held in place by inflated tip balloon 152, spokes 188 flex radially outward to form mesh fabric 190 into a bowl-shaped filter for trapping thrombus entering through gaps between the upper portions of spokes 188. The near end of filter tube 182 may be pulled while the remote end remains fixed to collapse filters 184 and 186 in preparation for the removal of filter tube 182 from the patient.

Reference is now made to FIGS. 9a–9d, which illustrate a method of surgically deploying single-limb graft 20. It is assumed that necessary mapping of the vessel and aneurysm 18 have been performed, and that an appropriately sized graft 20 has been selected and pre-loaded within a remote end of sheath passage 108 of appropriately sized deployment means 100. It is further assumed that certain equipment used for monitoring and visualization purposes is available for use by a surgeon skilled in the art, including a freely positionable C-arm having high resolution fluoroscopy, high quality angiography, and digital subtraction angiography capabilities.

Figure 9A:
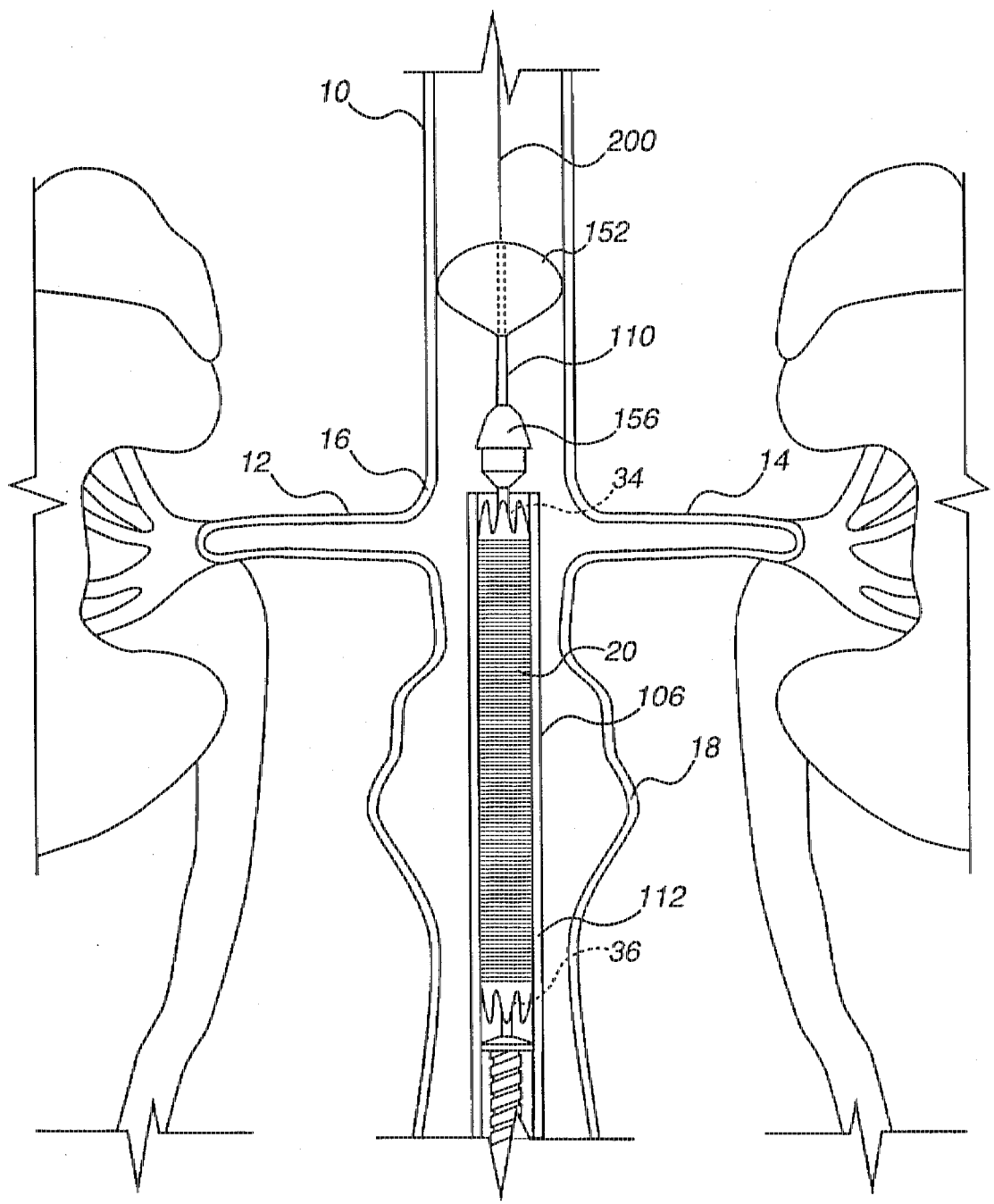
FIGS. 9a–9d are a series of elevational views illustrating a method of deploying a single-limb graft in accordance with the present invention.

As an initial step, the largest femoral artery, left or right, is determined by placing a high flow pig tail angiography catheter (not shown) through a percutaneous entry site in aorta 10 above aorto-renal junction 16 and taking an angiogram; the pig tail catheter is left in place. A flexible guide wire 200 preferably having a tip balloon (not shown) at its remote end is introduced into the vessel via a percutaneous entry site in the larger femoral artery, and progressively advanced upward until its tip balloon is above aorto-renal junction 16. Deployment means 100, pre-filled with heparinized solution through side port means 116, may then be introduced through the femoral entry site and caused to follow guide wire 200 by inserting a near end of the guide wire into first inner track 124 via first end port means 130, and slowly advancing deployment means 100 upward to the site of aneurysm 18. During advancement of deployment means 100 along guide wire 200, it is advantageous to maintain tip balloon 152 partially inflated with carbon dioxide for brighter visualization and atraumatic dilation of the vessel. In order to verify the position of renal arteries 12 and 14, contrast media is injected through first end port means 130 to the remote end opening of first inner track 124 above the renal arteries. At this point, deployment means 100 should be positioned such that proximal spring portion 34 is at or just below renal arteries 12 and 14, and distal spring portion 36 is above the bifurcated aorto-iliac junction and not within aneurysm 18. Blood flow through the region can be obstructed by inflating tip balloon 152 more fully using fluid injection means 142 so as to occlude aorta 10, as depicted in FIG. 9a. With aortic blood flow obstructed, deployment means 100 is rotated so that sheath introducer 106 and compressed graft 20 carried thereby are best aligned to match the bends in the patient's aorta.

Figure 9B:
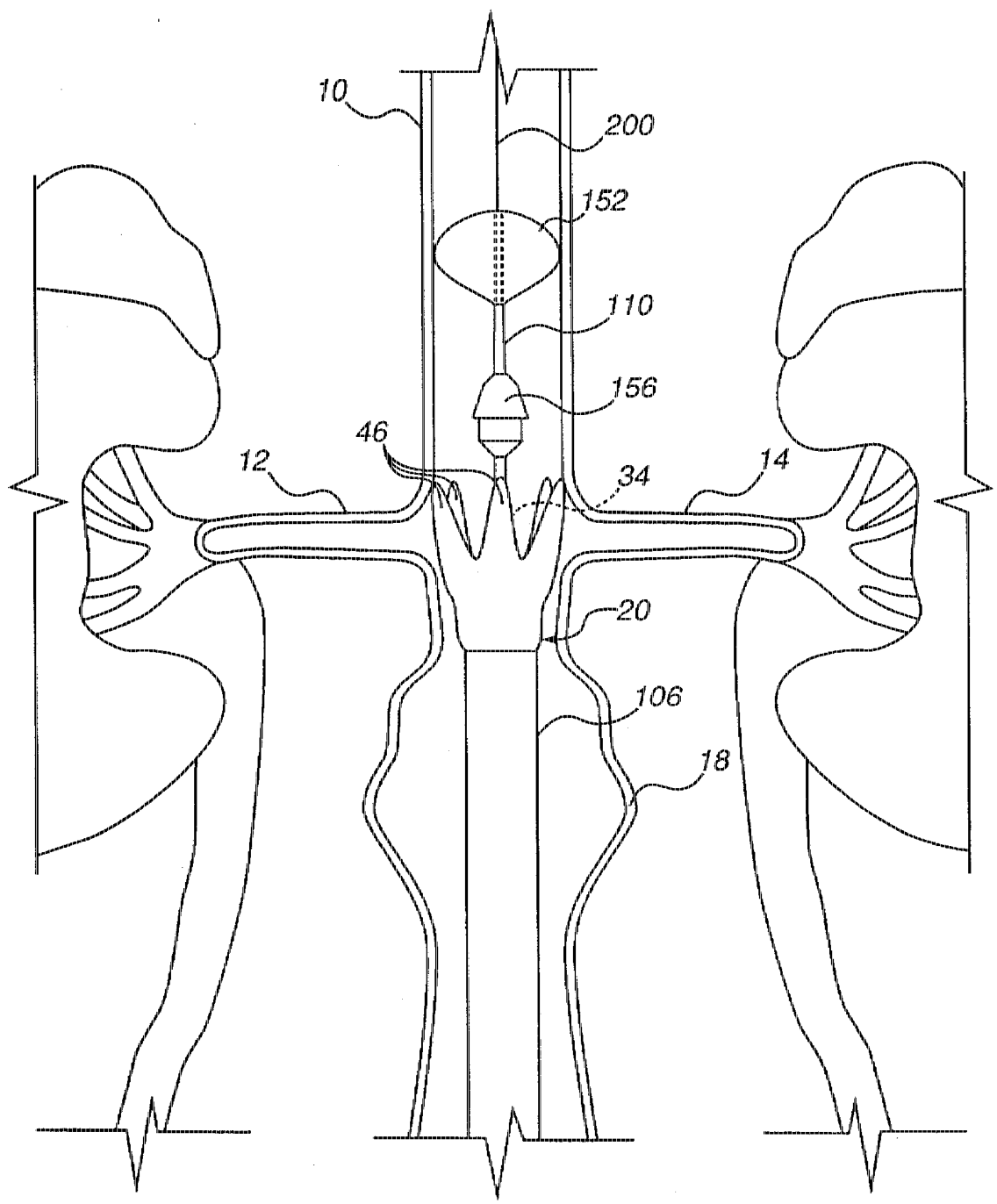
Figure 9C:
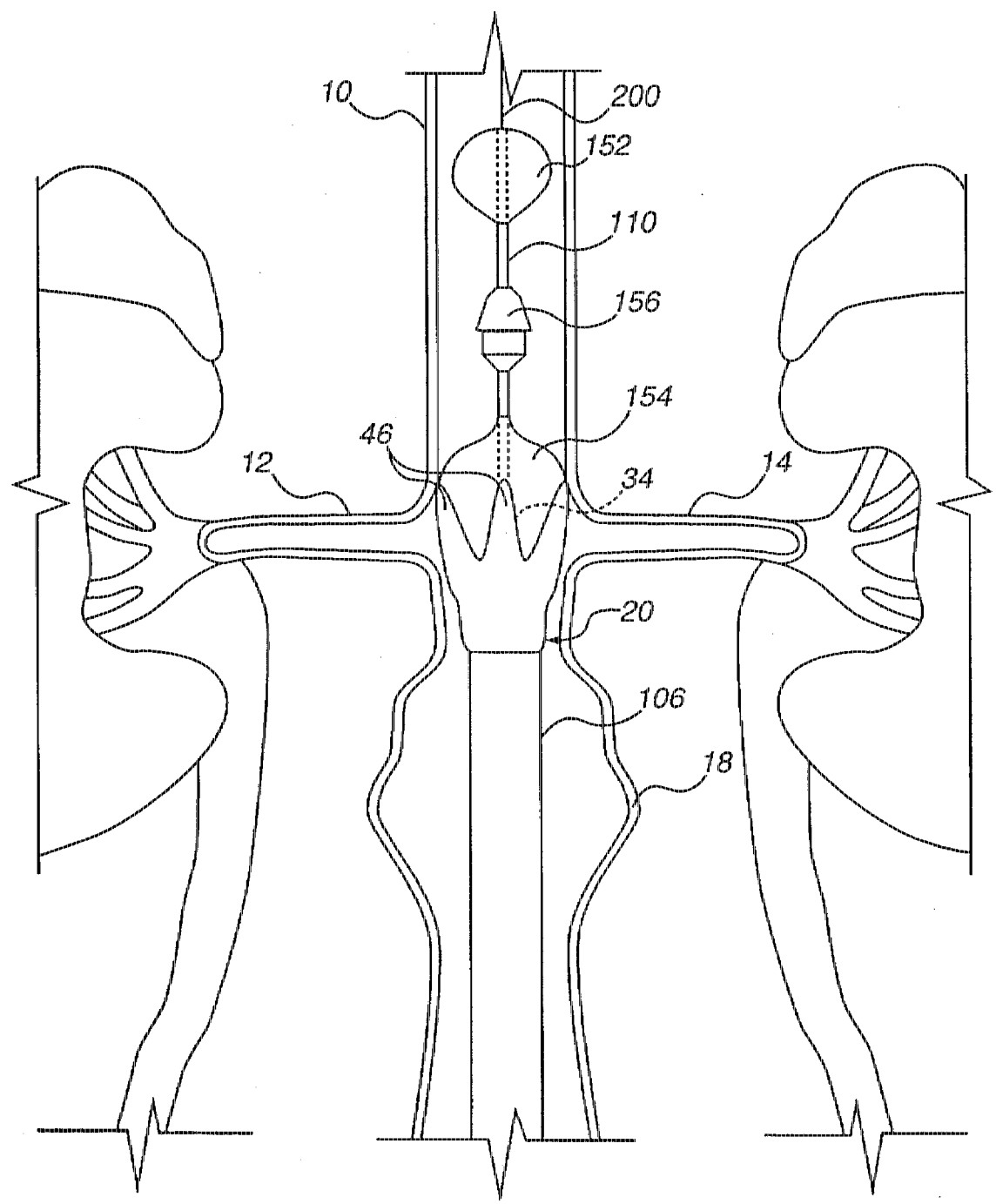

Deployment of proximal spring portion 34 is initiated by withdrawing sheath introducer 106 a short distance, approximately 3.5 cm, while simultaneously holding push rod 112 stationary. The finger portions 46 associated with proximal spring portion 34 will distend as the proximal spring portion is released from within sheath passage 108, and will appear as shown in FIG. 9b. Insertion catheter 110 is then advanced upward to position graft balloon 154 within recently deployed proximal spring portion 34, and the position and alignment of the proximal spring portion relative to renal arteries 12 and 14 is verified by further injection of contrast media through first end port means 130. Once proper verification has been made, graft balloon 154 is inflated to a relatively high pressure to create a smooth vessel wall seat for proximal spring portion 34 and forcibly model the spring portion into conforming fixed engagement with the interior surface of aorta 10 without causing inelastic deformation of the spring portion, as can be seen in FIG. 9c.

Figure 9D:
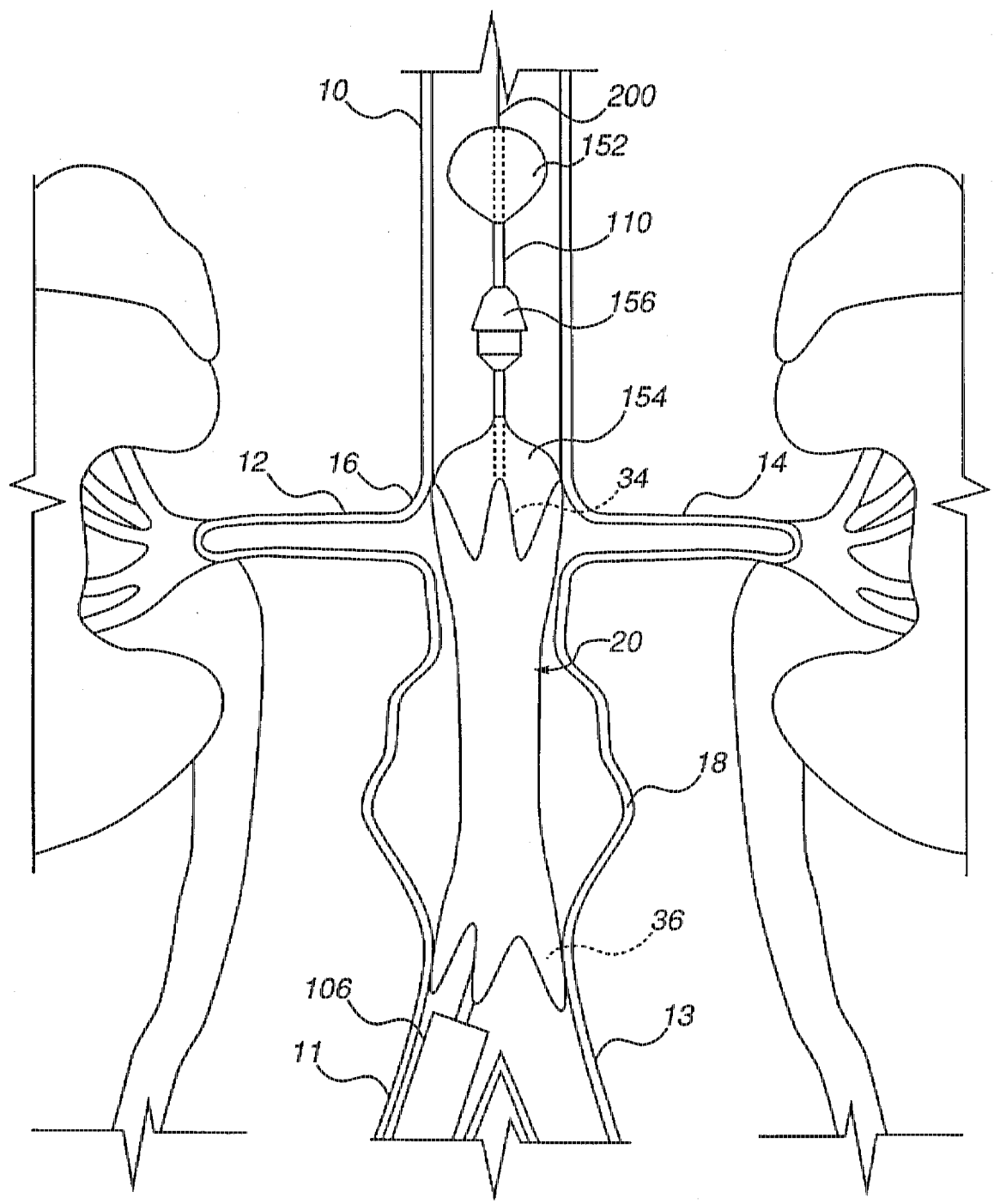

With inflated graft balloon 154 reinforcing fixation of proximal spring portion 34, sheath introducer 106 is further withdrawn to a point just before that which is required to release distal spring portion 36 from within sheath passage 108. Once verification has been made that distal spring portion 36 is not going to block either ipsilateral iliac vessel 11 or contralateral iliac vessel 13, sheath introducer may be withdrawn a distance sufficient to release distal spring portion 36 from within sheath passage 108, as depicted in FIG. 9d.

Blood flow may then be gently introduced to the newly deployed graft 20 by slowly deflating the graft balloon 154 in small increments. Graft balloon 154 may be repeatedly deflated, moved downward through graft 20 by increments of approximately 2 cm, and re-inflated to smooth out any wrinkles in graft material 24. After graft balloon 154 has travelled downward through graft 20 to within distal spring portion 36, it may again be inflated to a relatively high pressure to fix the distal spring portion in conformance with the interior surface of the vessel. As will be appreciated, expandable foam sleeves 58 (shown in FIG. 1 only) surrounding middle portion 29 act to promote clotting in an around aneurysm 18

If graft 20 is observed to be incorrectly placed and optional spool apparatus 170 has been provided, hand crank 178 thereof may be rotated very slowly in a counterclockwise direction as viewed in FIG. 7a to collapse distal spring portion 36 of graft 20 and reload graft 20 back to within sheath passage 108. The sheath may be pushed upward during reloading of graft 20 to reestablish an abutment seal between annular abutment lip 158 of tapered head 156 and the remote end of sheath introducer 106. Deployment means 100 may then be gently withdrawn, preferably after partially inflating tip balloon 152 with contrast media, such as carbon dioxide, for visualization. Verification that the removal process has not caused rupture of the vessel or embolization should be undertaken by way of an angiogram through the previously placed pig tail catheter.

Once graft 20 is correctly deployed, deployment means 100 and guide wire 200 may be completely withdrawn from the patient and the entry site attended using standard procedure. Where optional spool apparatus 170 is used, suture loops 174 may be removed by cutting them with blade 180 and rotating hand crank 178 in a counterclockwise direction. Tissue adhesive may then be released from light-degradable packets 56 (shown in FIG. 1 only) by insertion of a fiber optic catheter (not shown) through the femoral artery to graft 20 and direction of light at the packets, thereby helping to bond the graft to the vessel and seal micro-cracks which are a source of leakage. Post-operative CAT scan and ultrasound imaging may be conducted to verify isolation of the aneurysm, with particular attention being given to the occurrence of leaks at proximal spring portion 34 closest to the heart.

Figure 10A:
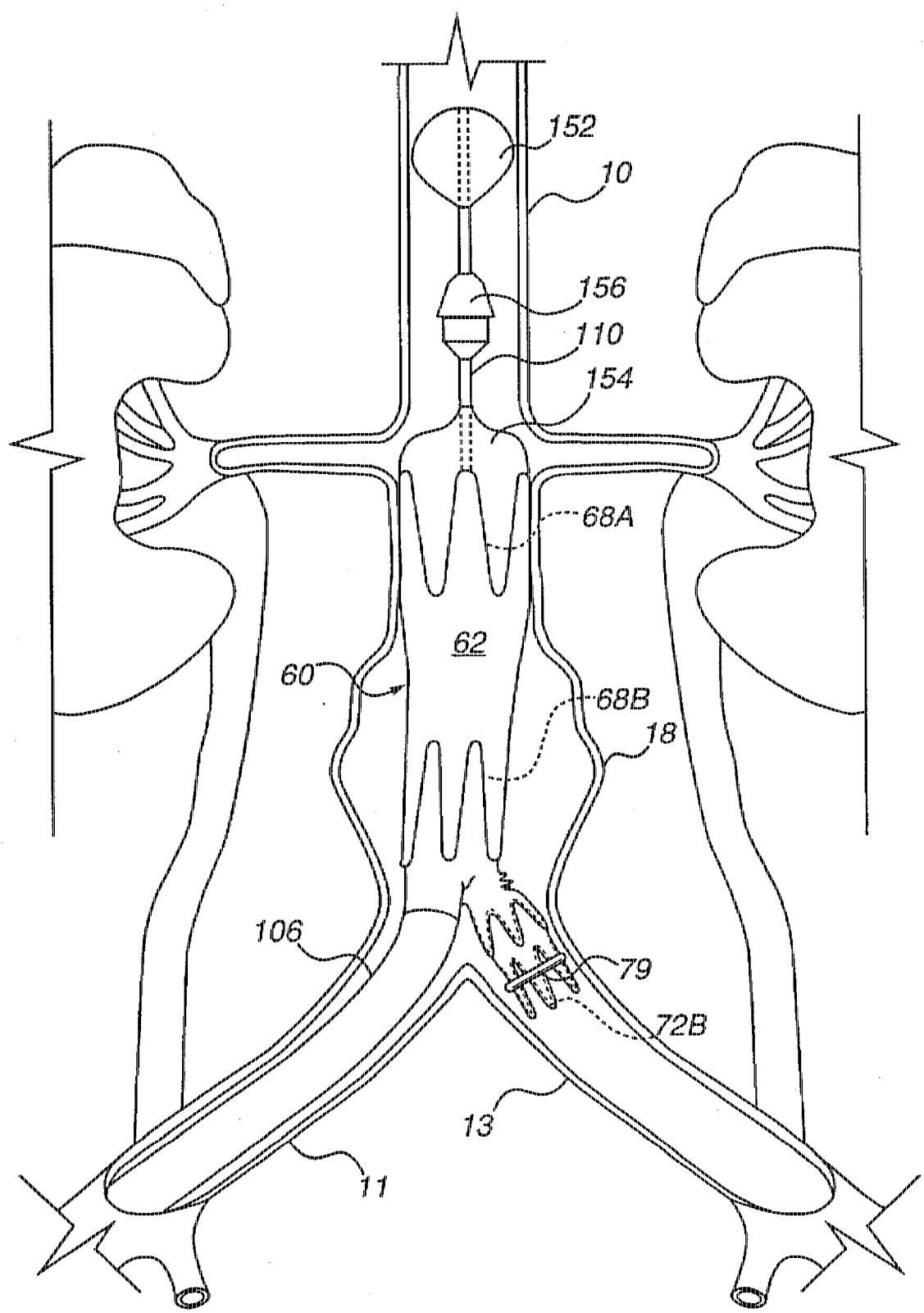
FIGS. 10a and 10b are elevational views illustrating a method of deploying a bifurcated graft in accordance with the present invention.
Figure 10B:
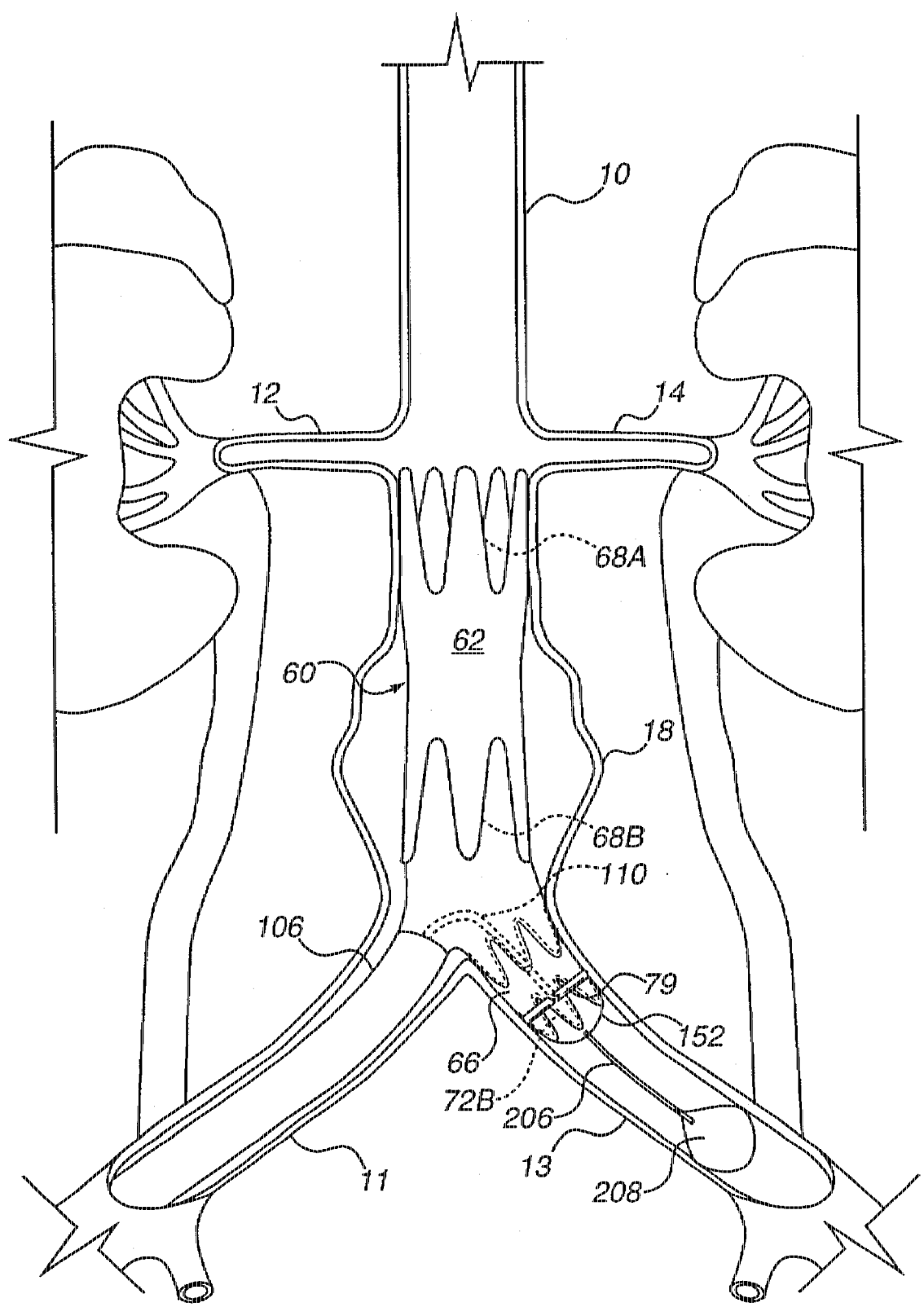

Referring now to FIGS. 10a and 10b, a single-entry method for deploying bifurcated graft 60 in accordance with the present invention is procedurally similar to the method described above with regard to single-limb graft 20, however additional steps are necessary to deploy contralateral limb 66 within contralateral iliac vessel 13 with the help of a deflectable-tip guide wire 206 used in place of regular guide wire 200 and having a controllable balloon 208 at a remote end thereof. Bifurcated graft 60 is pre-loaded into sheath passage 108 with contralateral limb 66 folded alongside primary limb 62, such that as sheath introducer 106 is withdrawn past graft junction 63 subsequent to deployment of proximal spring portion 68A, contralateral limb 66 unfolds generally into aneurysm 18 or the mouth of contralateral iliac vessel 13, as shown in FIG. 10a. Retainer ring 79 prevents premature expansion of distal spring portion 72B, thereby enabling distal spring portion 72B to be moved within contralateral iliac vessel 13 to a proper position for deployment.

To position distal spring portion 72B, graft balloon 154 is deflated and insertion catheter 110 with inserted deflectable guide wire 206 are withdrawn to the graft junction 63. A dial control (not shown) may be used to deflect the remote end of guide wire 206 and direct it into contralateral limb 66 of graft 60. Guide wire 206 may then be advanced deep into contralateral iliac vessel 13, and tip balloon 208 inflated sufficiently to fix the guide wire within the vessel. With its own tip balloon 152 partially inflated, insertion catheter 110 is advanced along fixed guide wire 206 into contralateral limb 66 between proximal spring portion 72A and distal spring portion 72B, after which the insertion catheter tip balloon 152 is inflated more fully to allow flow direction of blood to carry graft material 24 of the contralateral limb downward into contralateral iliac vessel 13. The distal end of contralateral limb 66 is moved to a final desired location by deflating the insertion catheter tip balloon 152 and advancing it to within distal spring portion 72B held by retainer ring 79, partially and carefully re-inflating tip balloon 152 to hold distal spring portion 72B by friction without breaking retainer ring 79, advancing insertion catheter 110 further into contralateral iliac vessel 13 until the distal end of contralateral limb 66 is at the desired location, and finally reinflating the tip balloon to a pressure sufficient to expand or break retainer ring 79 and release distal spring portion 72B, as shown in FIG. 10b. Deployment means 100 may then be withdrawn and removed from the patient and the entry site attended using standard procedure.

A method of coaxially coupling extension graft 80 to contralateral limb 66 in accordance with the present invention is once again similar to the method described above with regard to single-limb graft 20. While the present method is described herein for coupling extension graft 80 with contralateral limb 66, it will be understood that a similar procedure may be followed to deploy extension graft 80 in coupled relation with ipsilateral limb 64.

Figure 11:
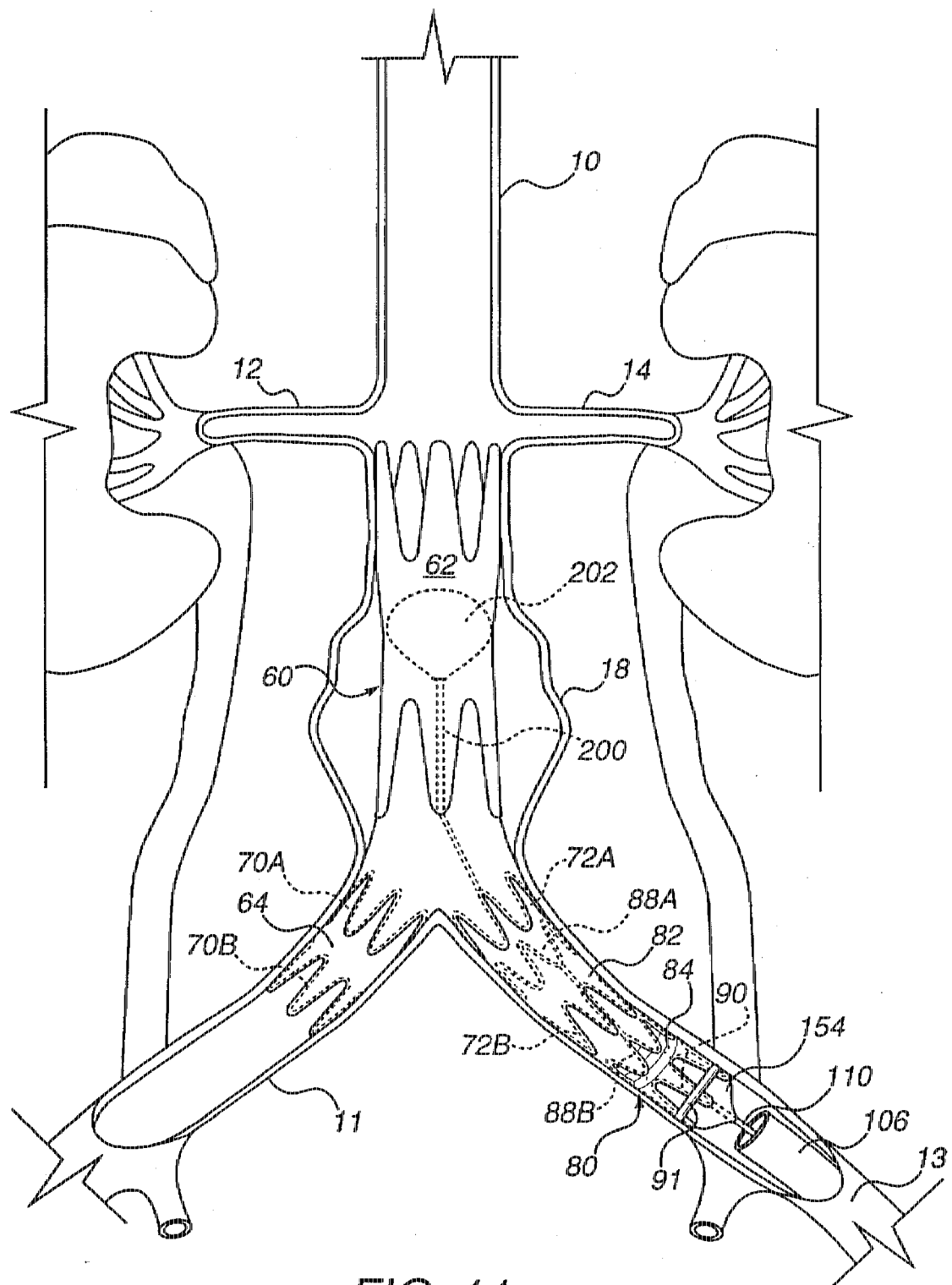
FIG. 11 is an elevational view illustrating a method of deploying an extension graft for coupling with a lateral limb of a bifurcated graft in accordance with the present invention.

Referring to FIG. 11, extension graft 80 is deployed via percutaneous entry through the contralateral femoral artery. A guide wire 200 having a controllable tip balloon 202 is advanced upward through contralateral limb 66 and into primary limb 62 of previously deployed bifurcated graft 60, and deployment means 100 carrying pre-loaded extension graft 80 is directed over guide wire 200, again using first inner track 124, and advanced to a position wherein mating portion 82 of extension graft 80 is partially within contralateral limb 66, preferably with first spring portion 88A of mating portion 82 overlapped by distal spring portion 72B of bifurcated graft 60. Sheath introducer 106 is then withdrawn while push rod 112 is held stationary in order to release first spring portion 88A. To set first spring portion 88A into conforming coupled engagement with an interior surface of contralateral limb 66, insertion catheter 110 is advanced upwards to locate graft balloon 154 within first spring portion 88A, and the graft balloon is inflated to a relatively high pressure. Contrast media may then be injected as previously described to verify that the coupled graft limbs are not leaking.

Next, sheath introducer 106 is further withdrawn to successively release second spring portion 88B and third spring portion 90 from sheath passage 108, with third spring portion 90 remaining in a compressed condition due to retainer ring 91. Graft balloon 154 is then deflated and moved downward to within third spring portion 90, and partially re-inflated to hold the third spring portion by friction, with care being taken so as not to overinflate graft balloon 154 and expand or break retainer ring 91. This permits the distal end of adjustable length portion 84 to be positioned generally just above the sub-iliac or hypo-gastric branch by further withdrawing insertion catheter 110. Third spring portion 90 is deployed by inflating graft balloon 154 therewithin to a relatively high pressure sufficient to expand or break surrounding retainer ring 91, as depicted in FIG. 11, and fix the third spring portion in conformance with the interior surface of contralateral iliac vessel 13. Any wrinkles in extension graft 80 may be removed using graft balloon 154 as previously described herein. Finally, once leakage has been ruled out, such as by angiogram verification, deployment means 100 may be withdrawn from the patient and the entry site attended.

What is claimed is:

1. An apparatus for engrafting a blood vessel comprising:
   a tubular graft of bio-compatible graft material for conducting fluid, said graft being capable of substantially deforming so as to conform to an interior surface of said blood vessel, said graft having proximal and distal opposite ends;
   radially compressible spring means for biasing said proximal and distal ends thereof radially outward into conforming fixed engagement with said interior surface of said blood vessel;
   said graft material being attached to said spring means and enclosing said spring means to prevent contact between said spring means and said interior surface of said vessel.

2. The apparatus according to claim 1, wherein said graft includes a middle portion extending between said proximal and distal ends, and said graft material is tapered to define a smaller fluid conducting area through said middle portion.

3. The apparatus according to claim 2, further comprising at least one medical-grade expandable foam cuff surrounding said middle portion.

4. The apparatus according to claim 1, wherein said spring means is a wire spring comprising a pair of annular spring portions spaced apart along a central axis for location at said proximal and distal ends of said graft, and at least one connecting bar extending between said spring portions for connecting said pair of spring portions to one another.

5. The apparatus according to claim 4, wherein said connecting bar is arranged to extend generally parallel to said central axis.

6. The apparatus according to claim 4, wherein each of said annular spring portions comprises a continuous zig-zag pattern of straight spokes connected by alternating crests and troughs, and said crests and troughs are of a predetermined radius.

7. The apparatus according to claim 6, wherein said graft material is cut out between said crests of at least one of said pair of spring portions to define a plurality of radially distensible finger portions.

8. The apparatus according to claim 7, further comprising a radially compressible anchor spring aligned generally on said central axis for fixing said graft within said blood vessel remotely of said proximal and distal ends of said graft.

9. The apparatus according to claim 8, wherein said anchor spring comprises a first annular spring portion attached to said graft material between said proximal and distal ends of said graft, and a second annular spring portion outside of said proximal and distal ends, said first and second spring portions being connected by at least one connecting bar extending generally parallel to said central axis.

10. The apparatus according to claim 1, further including tissue adhesive means associated with said proximal and distal ends of said graft for bonding said graft to said interior surface of said blood vessel and forming a substantially fluid-tight seal therebetween.

11. The apparatus according to claim 10, wherein said tissue adhesive means comprises a plurality of packets including a degradably photo-sensitive outer packet material enclosing a tissue adhesive, whereby said tissue adhesive may be released by directing a beam of light at said packets.

12. The apparatus according to claim 11, wherein said tissue adhesive substance is fibrin glue.

13. The apparatus according to claim 11, wherein said tissue adhesive substance is isobutyl 2 cyanoacrylate.

14. An apparatus for engrafting a bifurcated blood vessel comprising:
    a tubular graft of bio-compatible graft material for conducting fluid, said graft being capable of substantially deforming so as to conform to an interior surface of said blood vessel, said graft including a primary limb having proximal and distal opposite ends, an ipsilateral limb having proximal and distal opposite ends, and a contralateral limb having proximal and distal opposite ends, said proximal ends of said ipsilateral and contralateral limbs joining with said distal end of said primary limb for flow communication therewith to form a bifurcated fluid conduit;
    radially compressible spring means for biasing said proximal and distal ends of said primary, ipsilateral, and contralateral limbs radially outward into conforming fixed engagement with said interior surface of said blood vessel;
    said graft material being attached to said spring means and enclosing said spring means to prevent contact between said spring means and said interior surface of said blood vessel.

15. The apparatus according to claim 14, wherein said primary, ipsilateral, and contralateral limbs each include a middle portion extending between said proximal and distal ends thereof, and said graft material is tapered to define a smaller fluid conducting area through said middle portions.

16. The apparatus according to claim 15, further comprising at least one medical-grade expandable foam cuff surrounding said middle portion of said primary limb.

17. The apparatus according to claim 14, wherein said spring means comprises a plurality of wire springs associated one to each of said primary, ipsilateral, and contralateral limbs, each said wire spring having a proximal annular spring portion disposed at a proximal end of its associated limb and a distal annular spring portion disposed at a distal end of said associated limb, and at least one connecting bar extending between said spring portions for connecting said spring portions to one another.

18. The apparatus according to claim 17, wherein said at least one connecting bar is arranged to extend generally parallel to a central axis of said associated limb.

19. The apparatus according to claim 17, further comprising means for releasably retaining said distal spring portion of said contralateral limb in a radially compressed condition.

20. The apparatus according to claim 19, wherein said retaining means is an expandable retainer ring formed of suture material.

21. The apparatus according to claim 17, wherein each of said annular spring portions comprises a continuous zig-zag pattern of straight spokes connected by alternating crests and troughs, and said crests and troughs are of a predetermined radius.

22. The apparatus according to claim 21, wherein said graft material is cut out between said crests of said spring portion at said proximal end of said primary limb to define a plurality of radially distensible finger portions.

23. The apparatus according to claim 22, wherein said graft material is cut out between said crests of said spring portions at said distal ends of said ipsilateral and contralateral limbs to define a plurality of radially distensible finger portions.

24. The apparatus according to claim 14, further including tissue adhesive means associated with said proximal end of said primary limb for bonding said graft to said interior surface of said blood vessel and forming a substantially fluid-tight seal therebetween.

25. The apparatus according to claim 24, wherein said tissue adhesive means comprises a plurality of packets including a degradably photo-sensitive outer packet material enclosing a tissue adhesive, whereby said tissue adhesive may be released by directing a beam of light at said packets.

26. An apparatus for engrafting a blood vessel comprising:
    a tubular graft of bio-compatible graft material for conducting fluid, said graft being capable of substantially deforming so as to conform to an interior surface of said blood vessel, said graft including a mating portion having proximal and distal opposite ends and an adjustable length portion having proximal and distal opposite ends, said proximal end of said adjustable length portion being arranged adjacent to said distal end of said mating portion such that said mating and adjustable length portions extend along a common central axis; and
    radially compressible spring means for biasing said proximal end of said mating portion radially outward into conforming fixed engagement with an interior surface of another graft to which said apparatus is mated, and for biasing said distal end of said mating portion, said proximal end of said adjustable length portion, and said distal end of said adjustable length portion radially outward into conforming fixed engagement with said interior surface of said blood vessel, said spring means comprising a first annular spring portion associated with said proximal end of said mating portion, a second annular spring portion associated with said distal end of said mating portion and said proximal end of said adjustable length portion, said second spring portion being connected to said first spring portion by at least one connecting bar, and a third annular spring portion associated with said distal end of said adjustable length portion;

said graft material being attached to said spring means and enclosing said spring means to prevent contact between said spring means and said interior surface of said blood vessel, and said graft material being crimped along a length of said adjustable length portion, such that said third spring portion is axially movable relative to said second spring portion to adjust the length of said graft.

27. The apparatus according to claim 26, wherein said first and third spring portions comprise a continuous zig-zag pattern of straight spokes connected by alternating crests and troughs, and said graft material is cut out between said crests of said first and third spring portions to define a plurality of radially distensible finger portions.

28. The apparatus according to claim 26, further comprising retainer means for releasably retaining said third spring portion in a radially compressed condition.

* * * * *